E

(12) United States Patent
Albertsen et al.

(10) Patent No.: US 6,504,082 B1
(45) Date of Patent: Jan. 7, 2003

(54) ECDYSONE RECEPTORS AND METHODS FOR THEIR USE

(75) Inventors: Marc C. Albertsen, Grimes, IA (US); Catherine D. Brooke, Johnston, IA (US); Carl W. Garnaat, Ankeny, IA (US); Bradley Allen Roth, Urbandale, IA (US)

(73) Assignee: Pioneer Hi-Bred International, Inc., Des Moines, IA (US)

( * ) Notice: Subject to any disclaimer, the term of this patent is extended or adjusted under 35 U.S.C. 154(b) by 0 days.

(21) Appl. No.: 09/393,839

(22) Filed: Sep. 10, 1999

Related U.S. Application Data
(60) Provisional application No. 60/099,793, filed on Sep. 10, 1998.

(51) Int. Cl.[7] .......................... A01N 1/00; C12N 15/82; C12N 15/87
(52) U.S. Cl. .................. 800/278; 800/295; 800/320; 800/323.3
(58) Field of Search .................................. 435/468, 470, 435/272, 273; 800/320, 323.3, 288, 295, 278

(56) References Cited

U.S. PATENT DOCUMENTS

| | | |
|---|---|---|
| 4,833,080 A | 5/1989 | Brent et al. |
| 4,981,784 A | 1/1991 | Evans et al. |
| 5,071,773 A | 12/1991 | Evans et al. |
| 5,217,867 A | 6/1993 | Evans et al. |
| 5,310,662 A | 5/1994 | Evans et al. |
| 5,432,068 A | 7/1995 | Albertsen et al. |
| 5,478,369 A | 12/1995 | Albertsen et al. |
| 5,514,578 A | 5/1996 | Hogness et al. |
| 5,534,418 A | 7/1996 | Evans et al. |
| 5,554,510 A | 9/1996 | Hollis et al. |
| 5,571,696 A | 11/1996 | Evans et al. |
| 5,824,484 A | 10/1998 | Pfahl et al. |
| 5,824,524 A | 10/1998 | Albertsen et al. |
| 5,850,014 A | 12/1998 | Albertsen et al. |
| 5,859,341 A | 1/1999 | Albertsen et al. |
| 5,880,333 A | 3/1999 | Goff et al. |

FOREIGN PATENT DOCUMENTS

| | | |
|---|---|---|
| EP | 0465024 B1 | 1/1992 |
| WO | WO 90/11273 | 10/1990 |
| WO | 91/13167 | 9/1991 |
| WO | WO 92/16546 | 10/1992 |
| WO | WO 93/03162 | 2/1993 |
| WO | WO 93/11235 | 6/1993 |
| WO | WO 93/18380 | 9/1993 |
| WO | WO 93/21334 | 10/1993 |
| WO | WO 93/23431 | 11/1993 |
| WO | WO 94/01558 | 1/1994 |
| WO | 96/27673 | 9/1996 |
| WO | WO 96/37609 | 11/1996 |
| WO | WO 99/02683 | * 7/1998 |

OTHER PUBLICATIONS

Martinez et al., Creation of ecdysone receptor chimeras in plants for controlled regulation of gene expression, 1999, MOL GEN GENET, vol. 261, pp. 546–552.*

Chiu et al., Optimizing energy potentials for success in protein tertiary structure prediction, 1998, FOLDING & DESIGN, vol. 3, pp. 223–228.*

Ngo et al., Computational complexity, protein structure prediction, and the levinthal paradox, 1994, THE PROTEIN FOLDING PROBLEM AND TERTIARY STRUCTURE PREDICTION, pp. 491–494.*

Perera S. C. et al The ultraspiracle . . . expression of mRNA. 1998, Developmental Genetics, vol. 22, pp. 169–179.*

Trisyono et al. (1998) "Effect of the Ecdysone Agonists RH–2485 and Tebufenozide, on the Southwestern Corn Borer, *Diatraea grandiosella*", *Pestic. Sci.* 53:177–185.

Kothapalli et al. (1995) "Cloning and Developmental Expression of the Ecdysone Receptor Gene From The Spruce Budworm, *Choristoneura fumiferana*", *Developmental Genetics* 17:319–330.

Tzertinis et al. (1994) "BmCFI, a *Bombyx mori* RXR–type Receptor Related to the *Drosophilia ultraspiracle*", *J. Mol. Biol.* 238:479–486.

Swevers et al. (1996) "Bombys EcR (BmEcR) and Bombys USP (BmCF1) Combine to Form a Functional Ecdysone Receptor", *Insect Biochem. Molec. Biol.* 26(3):217–221.

Yao et al. (1993) "Functional Ecdysone Receptor is the Product of EcR and Ultraspiracle Genes", *Nature* 366:476–479.

Yao et al. (1992) "Drosophila Ultraspiracle Modulates Ecdysone Receptor Function Via Heterodimer Formation", *Cell* 71:63–72.

* cited by examiner

*Primary Examiner*—Dave T. Nguyen
*Assistant Examiner*—Brian Whiteman
(74) *Attorney, Agent, or Firm*—Alston & Bird LLP

(57) ABSTRACT

The field of the invention is inducible gene expression systems wherein expression is controlled by a novel ecdysone receptor or its derivatives. The field particularly relates to the isolation and characterization of nucleic acid and polypeptides for a novel ecdysone receptor. The nucleic acid and polypeptides are useful in novel gene expression systems inducible with ecdysone or derivative receptor agonists.

8 Claims, No Drawings

SEQUENCE LISTING

<160> NUMBER OF SEQ ID NOS: 8

<210> SEQ ID NO 1
<211> LENGTH: 2126
<212> TYPE: DNA
<213> ORGANISM: Ostrinia nubilalis
<220> FEATURE:
<221> NAME/KEY: CDS
<222> LOCATION: (368)..(2005)
<220> FEATURE:
<223> OTHER INFORMATION: Nucleotide sequence and deduced amino acid
      sequence of Ecdysone receptor -continued

```
<400> SEQUENCE: 1
gaattcggca cgaggtcgcg cgcgcgcaac gtgccactttt ttacggctca ccgcagtaac      60
ctcactgttc ctcaaacgcc ggacgaactc gactcgtggg actcgcgtgc tcttctcacc     120
tgttgcgtgg attgtgttgt gactagaaaa agttattgct gcaccatcaa accgtctcgt     180
cttattggag tgcaataaaa tcaagacagt ggattcgcct cggttccaaa gcggcataga     240
cgaatggtgt acgtctatag agtcgcgttt agatagttta gtgcggggaa aaagtgaagt     300
gaaagcctac gtcggaggat gtccgtcggc gattgtggat tccggagcgt atgacacgct     360
```

| | | | | | | | | | | | | | | | | |
|---|---|---|---|---|---|---|---|---|---|---|---|---|---|---|---|---|
| cgccgtc | atg | aga | cgc | cgc | tgg | tcg | aac | aac | gga | ggc | ttc | cag | acg | ctt | | 409 |
| | Met | Arg | Arg | Arg | Trp | Ser | Asn | Asn | Gly | Gly | Phe | Gln | Thr | Leu | | |
| | 1 | | | | 5 | | | | | 10 | | | | | | |
| cgt | atg | ctg | gag | gag | agc | tcg | tcc | gaa | gtg | aca | tcg | tcc | tct | gcc | ctc | 457 |
| Arg | Met | Leu | Glu | Glu | Ser | Ser | Ser | Glu | Val | Thr | Ser | Ser | Ser | Ala | Leu | |
| 15 | | | | | 20 | | | | | 25 | | | | | 30 | |
| ggt | ctt | cca | ccg | gcg | atg | gtt | atg | tca | ccg | gaa | tcg | ctg | gcg | tcg | cct | 505 |
| Gly | Leu | Pro | Pro | Ala | Met | Val | Met | Ser | Pro | Glu | Ser | Leu | Ala | Ser | Pro | |
| | | | | 35 | | | | | 40 | | | | | 45 | | |
| gag | tac | tcg | aat | ctc | gag | cta | tgg | gct | tac | gaa | gat | ggc | atc | tcg | tac | 553 |
| Glu | Tyr | Ser | Asn | Leu | Glu | Leu | Trp | Ala | Tyr | Glu | Asp | Gly | Ile | Ser | Tyr | |
| | 50 | | | | | 55 | | | | | 60 | | | | | |
| aat | acg | gct | cag | tcg | ttg | ctg | ggc | aac | gct | tgt | act | atg | caa | cag | cag | 601 |
| Asn | Thr | Ala | Gln | Ser | Leu | Leu | Gly | Asn | Ala | Cys | Thr | Met | Gln | Gln | Gln | |
| 65 | | | | | 70 | | | | | 75 | | | | | | |
| ccg | cct | aca | caa | ccc | ctg | cct | tcg | atg | ccc | tta | ccg | atg | cca | ccc | acg | 649 |
| Pro | Pro | Thr | Gln | Pro | Leu | Pro | Ser | Met | Pro | Leu | Pro | Met | Pro | Pro | Thr | |
| | 80 | | | | | 85 | | | | | 90 | | | | | |
| acg | cct | aaa | tct | gag | aac | gag | tca | atg | tca | tca | ggc | cga | gaa | gaa | ttg | 697 |
| Thr | Pro | Lys | Ser | Glu | Asn | Glu | Ser | Met | Ser | Ser | Gly | Arg | Glu | Glu | Leu | |
| 95 | | | | | 100 | | | | | 105 | | | | | 110 | |
| tca | cca | gct | tcg | agc | gta | aac | ggt | tgc | agt | aca | gat | ggc | gag | gca | aga | 745 |
| Ser | Pro | Ala | Ser | Ser | Val | Asn | Gly | Cys | Ser | Thr | Asp | Gly | Glu | Ala | Arg | |
| | | | | 115 | | | | | 120 | | | | | 125 | | |
| cgg | cag | aaa | aag | ggg | ccc | gcg | cct | cgc | cag | cag | gag | gaa | tta | tgt | ctc | 793 |
| Arg | Gln | Lys | Lys | Gly | Pro | Ala | Pro | Arg | Gln | Gln | Glu | Glu | Leu | Cys | Leu | |
| | | | 130 | | | | | 135 | | | | | 140 | | | |
| gtc | tgc | ggc | gac | aga | gcc | tcc | gga | tac | cat | tac | aac | gcg | ctt | acg | tgt | 841 |
| Val | Cys | Gly | Asp | Arg | Ala | Ser | Gly | Tyr | His | Tyr | Asn | Ala | Leu | Thr | Cys | |
| | 145 | | | | | 150 | | | | | 155 | | | | | |
| gaa | gga | tgc | aaa | ggt | ttc | ttc | agg | cgg | agt | gtg | acc | aaa | aat | gcg | gtg | 889 |
| Glu | Gly | Cys | Lys | Gly | Phe | Phe | Arg | Arg | Ser | Val | Thr | Lys | Asn | Ala | Val | |
| 160 | | | | | 165 | | | | | 170 | | | | | | |
| tac | att | tgc | aag | ttt | ggg | cat | gcg | tgc | gaa | atg | gac | atg | tat | atg | cgg | 937 |
| Tyr | Ile | Cys | Lys | Phe | Gly | His | Ala | Cys | Glu | Met | Asp | Met | Tyr | Met | Arg | |
| 175 | | | | | 180 | | | | | 185 | | | | | 190 | |
| cgg | aaa | tgt | caa | gaa | tgc | cgg | ttg | aag | aag | tgt | tta | gcg | gtg | ggc | atg | 985 |
| Arg | Lys | Cys | Gln | Glu | Cys | Arg | Leu | Lys | Lys | Cys | Leu | Ala | Val | Gly | Met | |
| | | | | 195 | | | | | 200 | | | | | 205 | | |
| agg | ccc | gag | tgc | gtg | gtg | cca | gaa | acg | cag | tgt | gcg | caa | aaa | agg | aaa | 1033 |
| Arg | Pro | Glu | Cys | Val | Val | Pro | Glu | Thr | Gln | Cys | Ala | Gln | Lys | Arg | Lys | |
| | | | 210 | | | | | 215 | | | | | 220 | | | |
| gag | aag | aaa | gca | cag | aga | gaa | aaa | gac | aaa | cta | cca | gtg | agc | aca | acg | 1081 |
| Glu | Lys | Lys | Ala | Gln | Arg | Glu | Lys | Asp | Lys | Leu | Pro | Val | Ser | Thr | Thr | |
| | 225 | | | | | 230 | | | | | 235 | | | | | |
| aca | gta | gac | gat | cat | atg | ccc | cca | atc | atg | cag | tgt | gat | ccg | cca | ccc | 1129 |
| Thr | Val | Asp | Asp | His | Met | Pro | Pro | Ile | Met | Gln | Cys | Asp | Pro | Pro | Pro | |
| 240 | | | | | 245 | | | | | 250 | | | | | | |

-continued

| | |
|---|---|
| ccg gag gca gcg agg att ctg gaa tgt ttg cag cat gaa gtg gtc ccg<br>Pro Glu Ala Ala Arg Ile Leu Glu Cys Leu Gln His Glu Val Val Pro<br>255                    260                265              270 | 1177 |
| cgg ttc ctc tcg gag aag ctg atg gag cag aat cgg ttg aag aac ata<br>Arg Phe Leu Ser Glu Lys Leu Met Glu Gln Asn Arg Leu Lys Asn Ile<br>               275                280              285 | 1225 |
| ccc ccc ctc acc gcc aac cag cag ttc ctg atc gcg agg ctg gtg tgg<br>Pro Pro Leu Thr Ala Asn Gln Gln Phe Leu Ile Ala Arg Leu Val Trp<br>           290                295              300 | 1273 |
| tac cag gac gga tac gag cag cct tcg gaa gag gat ctc aaa agg gtg<br>Tyr Gln Asp Gly Tyr Glu Gln Pro Ser Glu Glu Asp Leu Lys Arg Val<br>305                    310                315 | 1321 |
| acg cag act tgg caa tca gca gat gaa gaa gac gaa gac tca gac atg<br>Thr Gln Thr Trp Gln Ser Ala Asp Glu Glu Asp Glu Asp Ser Asp Met<br>320                    325                330 | 1369 |
| cca ttc cgc cag atc aca gaa atg acc atc ctc aca gta cag cta ata<br>Pro Phe Arg Gln Ile Thr Glu Met Thr Ile Leu Thr Val Gln Leu Ile<br>335                    340                345              350 | 1417 |
| gtc gag ttt gcc aaa ggc cta cct ggt ttc tca aag atc tca caa cct<br>Val Glu Phe Ala Lys Gly Leu Pro Gly Phe Ser Lys Ile Ser Gln Pro<br>           355                360              365 | 1465 |
| gac cag atc aca tta tta aag gca tgc tca agc gaa gtg atg atg ctc<br>Asp Gln Ile Thr Leu Leu Lys Ala Cys Ser Ser Glu Val Met Met Leu<br>           370                375              380 | 1513 |
| cga gta gcg agg cgg tac gac gcg gtg tcg gat agc gtt ctg ttc gcc<br>Arg Val Ala Arg Arg Tyr Asp Ala Val Ser Asp Ser Val Leu Phe Ala<br>385                    390                395 | 1561 |
| aac aac cag gcg tac act cgc gac aac tac cgc aag gcg ggc atg gcg<br>Asn Asn Gln Ala Tyr Thr Arg Asp Asn Tyr Arg Lys Ala Gly Met Ala<br>400                    405                410 | 1609 |
| tac gtc atc gag gac ctg ctg cac ttc tgc cgc tgc atg tac tcg atg<br>Tyr Val Ile Glu Asp Leu Leu His Phe Cys Arg Cys Met Tyr Ser Met<br>415                    420                425              430 | 1657 |
| tcg atg gac aac gtg cat tac gcg ctc ctc act gcc atc gtt ata ttc<br>Ser Met Asp Asn Val His Tyr Ala Leu Leu Thr Ala Ile Val Ile Phe<br>           435                440              445 | 1705 |
| tcg gat cgg ccg ggc cta gag cag cca cag cta gta gaa gag atc cag<br>Ser Asp Arg Pro Gly Leu Glu Gln Pro Gln Leu Val Glu Glu Ile Gln<br>           450                455              460 | 1753 |
| cgg tat tac ctg aac acg ctg cgg gtg tac atc atg aac cag cac agc<br>Arg Tyr Tyr Leu Asn Thr Leu Arg Val Tyr Ile Met Asn Gln His Ser<br>465                    470                475 | 1801 |
| gcg tcg cca cgc tgc gcc gtc atc tac gcg aag att ctg tcg gtg ctt<br>Ala Ser Pro Arg Cys Ala Val Ile Tyr Ala Lys Ile Leu Ser Val Leu<br>480                    485                490 | 1849 |
| acc gag ttg cgg acg ctg ggc atg cag aat tcg aac atg tgc atc tcg<br>Thr Glu Leu Arg Thr Leu Gly Met Gln Asn Ser Asn Met Cys Ile Ser<br>495                    500                505              510 | 1897 |
| ctg aag ctc aag aac agg aag ctg ccg ccg ttc ctg gag gag att tgg<br>Leu Lys Leu Lys Asn Arg Lys Leu Pro Pro Phe Leu Glu Glu Ile Trp<br>           515                520              525 | 1945 |
| gac gtg gcc gac gtg tcg acg gcg cag gcg ccg ctg gtg gcc gac ggc<br>Asp Val Ala Asp Val Ser Thr Ala Gln Ala Pro Leu Val Ala Asp Gly<br>           530                535              540 | 1993 |
| gct acg gcg ctc tagccccgcc cacgcgatcg cgccgcctcg cccgcgcccc<br>Ala Thr Ala Leu<br>545 | 2045 |
| gcggcttgct ctagcgtagt gatgggactc ggaaaaataa ctcgatttaa cccgagctaa | 2105 |
| aattcacgta actcggttaa c | 2126 |

<210> SEQ ID NO 2
<211> LENGTH: 546
<212> TYPE: PRT
<213> ORGANISM: Ostrinia nubilalis

<400> SEQUENCE: 2

```
Met Arg Arg Arg Trp Ser Asn Asn Gly Gly Phe Gln Thr Leu Arg Met
  1               5                  10                  15

Leu Glu Glu Ser Ser Ser Glu Val Thr Ser Ser Ser Ala Leu Gly Leu
             20                  25                  30

Pro Pro Ala Met Val Met Ser Pro Glu Ser Leu Ala Ser Pro Glu Tyr
         35                  40                  45

Ser Asn Leu Glu Leu Trp Ala Tyr Glu Asp Gly Ile Ser Tyr Asn Thr
     50                  55                  60

Ala Gln Ser Leu Leu Gly Asn Ala Cys Thr Met Gln Gln Gln Pro Pro
 65                  70                  75                  80

Thr Gln Pro Leu Pro Ser Met Pro Leu Pro Met Pro Pro Thr Thr Pro
                 85                  90                  95

Lys Ser Glu Asn Glu Ser Met Ser Ser Gly Arg Glu Glu Leu Ser Pro
            100                 105                 110

Ala Ser Ser Val Asn Gly Cys Ser Thr Asp Gly Glu Ala Arg Arg Gln
        115                 120                 125

Lys Lys Gly Pro Ala Pro Arg Gln Gln Glu Glu Leu Cys Leu Val Cys
    130                 135                 140

Gly Asp Arg Ala Ser Gly Tyr His Tyr Asn Ala Leu Thr Cys Glu Gly
145                 150                 155                 160

Cys Lys Gly Phe Phe Arg Arg Ser Val Thr Lys Asn Ala Val Tyr Ile
                165                 170                 175

Cys Lys Phe Gly His Ala Cys Glu Met Asp Met Tyr Met Arg Arg Lys
            180                 185                 190

Cys Gln Glu Cys Arg Leu Lys Lys Cys Leu Ala Val Gly Met Arg Pro
        195                 200                 205

Glu Cys Val Val Pro Glu Thr Gln Cys Ala Gln Lys Arg Lys Glu Lys
    210                 215                 220

Lys Ala Gln Arg Glu Lys Asp Lys Leu Pro Val Ser Thr Thr Thr Val
225                 230                 235                 240

Asp Asp His Met Pro Pro Ile Met Gln Cys Asp Pro Pro Pro Pro Glu
                245                 250                 255

Ala Ala Arg Ile Leu Glu Cys Leu Gln His Glu Val Val Pro Arg Phe
            260                 265                 270

Leu Ser Glu Lys Leu Met Glu Gln Asn Arg Leu Lys Asn Ile Pro Pro
        275                 280                 285

Leu Thr Ala Asn Gln Gln Phe Leu Ile Ala Arg Leu Val Trp Tyr Gln
    290                 295                 300

Asp Gly Tyr Glu Gln Pro Ser Glu Glu Asp Leu Lys Arg Val Thr Gln
305                 310                 315                 320

Thr Trp Gln Ser Ala Asp Glu Glu Asp Glu Asp Ser Asp Met Pro Phe
                325                 330                 335

Arg Gln Ile Thr Glu Met Thr Ile Leu Thr Val Gln Leu Ile Val Glu
            340                 345                 350

Phe Ala Lys Gly Leu Pro Gly Phe Ser Lys Ile Ser Gln Pro Asp Gln
        355                 360                 365

Ile Thr Leu Leu Lys Ala Cys Ser Ser Glu Val Met Met Leu Arg Val
```

-continued

```
                           370                 375                 380
Ala Arg Arg Tyr Asp Ala Val Ser Asp Ser Val Leu Phe Ala Asn Asn
385                 390                 395                 400

Gln Ala Tyr Thr Arg Asp Asn Tyr Arg Lys Ala Gly Met Ala Tyr Val
                405                 410                 415

Ile Glu Asp Leu Leu His Phe Cys Arg Cys Met Tyr Ser Met Ser Met
                420                 425                 430

Asp Asn Val His Tyr Ala Leu Leu Thr Ala Ile Val Ile Phe Ser Asp
                435                 440                 445

Arg Pro Gly Leu Glu Gln Pro Gln Leu Val Glu Glu Ile Gln Arg Tyr
            450                 455                 460

Tyr Leu Asn Thr Leu Arg Val Tyr Ile Met Asn Gln His Ser Ala Ser
465                 470                 475                 480

Pro Arg Cys Ala Val Ile Tyr Ala Lys Ile Leu Ser Val Leu Thr Glu
                485                 490                 495

Leu Arg Thr Leu Gly Met Gln Asn Ser Asn Met Cys Ile Ser Leu Lys
                500                 505                 510

Leu Lys Asn Arg Lys Leu Pro Pro Phe Leu Glu Glu Ile Trp Asp Val
                515                 520                 525

Ala Asp Val Ser Thr Ala Gln Ala Pro Leu Val Ala Asp Gly Ala Thr
                530                 535                 540

Ala Leu
545
```

<210> SEQ ID NO 3
<211> LENGTH: 1837
<212> TYPE: DNA
<213> ORGANISM: Ostrinia nubilalis
<220> FEATURE:
<221> NAME/KEY: CDS
<222> LOCATION: (224)..(1603)
<220> FEATURE:
<223> OTHER INFORMATION: Nucleotide sequence and deduced amino acid
      sequence of Ultraspiracle

<400> SEQUENCE: 3

```
ccgctcgcgc tcgctcgatc gccttctctg taatttagag ccttaatcgt cacagtcaca    60
agttcacgac tcgcggattt gattcggcag ggcgcaaatt gatcgtgaag atcgtgtcgg   120
tgagacgcgg gccgttggat tttccgtgtg aatccgtgca ttatattggt gctcgcttat   180
gtgcagtggg ttgctagtga tgtgaggatg ctagtgcgtg gcc atg tct agc gtg    235
                                              Met Ser Ser Val
                                                 1 gcg aag aaa gac aag ccc acg atg tct gtg acg gcg ctg atc aac tgg   283
Ala Lys Lys Asp Lys Pro Thr Met Ser Val Thr Ala Leu Ile Asn Trp
 5                  10                  15                  20 gcg cgg ccg ccg ccg ccg ggg ccg cag cag ccg ccg ccc gcg act aac   331
Ala Arg Pro Pro Pro Pro Gly Pro Gln Gln Pro Pro Pro Ala Thr Asn
                25                  30                  35 ctc ctg caa ccg ttc gca atg cca tcc acc att ccc agc gtc gac tgc   379
Leu Leu Gln Pro Phe Ala Met Pro Ser Thr Ile Pro Ser Val Asp Cys
            40                  45                  50 tcc ctc gac atg caa tgg tta aac ctg gag agc agc ttc atg tcg ccg   427
Ser Leu Asp Met Gln Trp Leu Asn Leu Glu Ser Ser Phe Met Ser Pro
        55                  60                  65 atg tcc ccg cct gag atg aag ccc gac aca gcc atg ctg gac ggg ctc   475
Met Ser Pro Pro Glu Met Lys Pro Asp Thr Ala Met Leu Asp Gly Leu
 70                  75                  80
```

-continued

| | | |
|---|---|---|
| cgg gat gac gcg acc tcc ccc ccg gcc ttc aag aac tac ccc ccc aat<br>Arg Asp Asp Ala Thr Ser Pro Pro Ala Phe Lys Asn Tyr Pro Pro Asn<br>85                                   90                            95                           100 | 523 |

```
cgg gat gac gcg acc tcc ccc ccg gcc ttc aag aac tac ccc ccc aat        523
Arg Asp Asp Ala Thr Ser Pro Pro Ala Phe Lys Asn Tyr Pro Pro Asn
 85                  90                  95                 100 cac cca ctg agc ggg tcg aaa cac ctc tgc tca ata tgc gga gac agg        571
His Pro Leu Ser Gly Ser Lys His Leu Cys Ser Ile Cys Gly Asp Arg
                105                 110                 115 gcc tcg ggg aaa cac tac gga gta tac agt tgc gaa ggc tgc aaa ggg        619
Ala Ser Gly Lys His Tyr Gly Val Tyr Ser Cys Glu Gly Cys Lys Gly
            120                 125                 130 ttc ttc aag agg aca gta cgg aag gac ctc aca tac gcg tgt cgc gaa        667
Phe Phe Lys Arg Thr Val Arg Lys Asp Leu Thr Tyr Ala Cys Arg Glu
        135                 140                 145 gaa cgg aat tgc atc atc gac aag cga cag agg aat aga tgc cag tac        715
Glu Arg Asn Cys Ile Ile Asp Lys Arg Gln Arg Asn Arg Cys Gln Tyr
    150                 155                 160 tgt cga tat cag aaa tgt ctg gcg tgc ggc atg aag cgc gag gca gtg        763
Cys Arg Tyr Gln Lys Cys Leu Ala Cys Gly Met Lys Arg Glu Ala Val
165                 170                 175                 180 cag gag gag cgg cag cgg gca gct agg ggg aca gag gat gct cac ccg        811
Gln Glu Glu Arg Gln Arg Ala Ala Arg Gly Thr Glu Asp Ala His Pro
                185                 190                 195 agc agt tct gta cag gag ctg tcg atc gag cgg ctg ctg gag atg gag        859
Ser Ser Ser Val Gln Glu Leu Ser Ile Glu Arg Leu Leu Glu Met Glu
            200                 205                 210 tcg cta gtg gca gac acc agc gag gag tgc cag ttc ctg cgg gtc ggg        907
Ser Leu Val Ala Asp Thr Ser Glu Glu Cys Gln Phe Leu Arg Val Gly
        215                 220                 225 ccc gac agc aac gtg ccc ccc aag ttc cgc gct ccc gtc tct agc ctt        955
Pro Asp Ser Asn Val Pro Pro Lys Phe Arg Ala Pro Val Ser Ser Leu
    230                 235                 240 tgt caa ata ggt aac aaa caa atc gcg gcg ctg gtg gtg tgg gcg cgc       1003
Cys Gln Ile Gly Asn Lys Gln Ile Ala Ala Leu Val Val Trp Ala Arg
245                 250                 255                 260 gac atc ccg cac ttc ggg cag ctg gag atg gag gac cag gtg ctg ctc       1051
Asp Ile Pro His Phe Gly Gln Leu Glu Met Glu Asp Gln Val Leu Leu
                265                 270                 275 atc aag agc gcg tgg aac gag ctg ctc ctc ttc gcg ata gcg tgg cgc       1099
Ile Lys Ser Ala Trp Asn Glu Leu Leu Leu Phe Ala Ile Ala Trp Arg
            280                 285                 290 tcg atg gag ttc ctg acg gat gag cgt gaa aac atg gac ggc acg cga       1147
Ser Met Glu Phe Leu Thr Asp Glu Arg Glu Asn Met Asp Gly Thr Arg
        295                 300                 305 agc tct tcg ccg cca cag ctc atg tgc ttg atg cct ggc atg acg ctg       1195
Ser Ser Ser Pro Pro Gln Leu Met Cys Leu Met Pro Gly Met Thr Leu
    310                 315                 320 cac cgc aac tcg gcg ctg cag gcg ggc gtg ggg cag atc ttc gac cgc       1243
His Arg Asn Ser Ala Leu Gln Ala Gly Val Gly Gln Ile Phe Asp Arg
325                 330                 335                 340 gtg ctg tcg gag ctg tcg ctg aag atg cgc gcg ctg cgc atg gac cag       1291
Val Leu Ser Glu Leu Ser Leu Lys Met Arg Ala Leu Arg Met Asp Gln
                345                 350                 355 gcc gag tac gtc gcg ctc aag gcc atc atc ctg ctc aac ccg gat gta       1339
Ala Glu Tyr Val Ala Leu Lys Ala Ile Ile Leu Leu Asn Pro Asp Val
            360                 365                 370 aaa gga ttg aag aac cgt cag gag gtc gaa gta ctg cgg gaa aag atg       1387
Lys Gly Leu Lys Asn Arg Gln Glu Val Glu Val Leu Arg Glu Lys Met
        375                 380                 385 tac tcg tgc ctc gac gag tac tgc cgg cgc tcg cgc ggc acc gag gag       1435
Tyr Ser Cys Leu Asp Glu Tyr Cys Arg Arg Ser Arg Gly Thr Glu Glu
    390                 395                 400
```

-continued

```
ggc cgc ttt gcg tcg ctg ctg cgg ctg ccg gcg ctg cgc tcc atc    1483
Gly Arg Phe Ala Ser Leu Leu Arg Leu Pro Ala Leu Arg Ser Ile
405             410                 415                 420 tcg ctc aag agc ttc gag cac ctg ttc ttc cac ctc gtc gcc gac    1531
Ser Leu Lys Ser Phe Glu His Leu Phe Phe His Leu Val Ala Asp
            425                 430                 435 gcc tcc atc gcc gcc tac atc cgc gac gcg ctg cgc acg cac gcg ccg  1579
Ala Ser Ile Ala Ala Tyr Ile Arg Asp Ala Leu Arg Thr His Ala Pro
        440                 445                 450 cct atc gac gcc tcc gcc atg ctg taggaagcta ttgtaagaca agtcgactac  1633
Pro Ile Asp Ala Ser Ala Met Leu
            455                 460 gtgtcaccag tcgacaatca atgctgtgtg tattgacgcc tcggccatac tctaggaagc  1693
tattgtaaga caagtcggct acgtgtcacc agtcgacaat caatgctgtg tgtattgacg  1753
cctccgccat gctgtaggaa acgactatac gagtcatatc accagtcgtc aatcaacgtg  1813
atgtgtatgt tgatgcctcg gcca                                       1837
```

<210> SEQ ID NO 4
<211> LENGTH: 460
<212> TYPE: PRT
<213> ORGANISM: Ostrinia nubilalis

<400> SEQUENCE: 4

```
Met Ser Ser Val Ala Lys Lys Asp Lys Pro Thr Met Ser Val Thr Ala
 1               5                  10                  15

Leu Ile Asn Trp Ala Arg Pro Pro Pro Gly Pro Gln Gln Pro Pro
                20                  25                  30

Pro Ala Thr Asn Leu Leu Gln Pro Phe Ala Met Pro Ser Thr Ile Pro
            35                  40                  45

Ser Val Asp Cys Ser Leu Asp Met Gln Trp Leu Asn Leu Glu Ser Ser
        50                  55                  60

Phe Met Ser Pro Met Ser Pro Pro Glu Met Lys Pro Asp Thr Ala Met
65                  70                  75                  80

Leu Asp Gly Leu Arg Asp Asp Ala Thr Ser Pro Pro Ala Phe Lys Asn
                85                  90                  95

Tyr Pro Pro Asn His Pro Leu Ser Gly Lys His Leu Cys Ser Ile
            100                 105                 110

Cys Gly Asp Arg Ala Ser Gly Lys His Tyr Gly Val Tyr Ser Cys Glu
        115                 120                 125

Gly Cys Lys Gly Phe Phe Lys Arg Thr Val Arg Lys Asp Leu Thr Tyr
    130                 135                 140

Ala Cys Arg Glu Glu Arg Asn Cys Ile Ile Asp Lys Arg Gln Arg Asn
145                 150                 155                 160

Arg Cys Gln Tyr Cys Arg Tyr Gln Lys Cys Leu Ala Cys Gly Met Lys
                165                 170                 175

Arg Glu Ala Val Gln Glu Glu Arg Gln Arg Ala Ala Arg Gly Thr Glu
            180                 185                 190

Asp Ala His Pro Ser Ser Val Gln Glu Leu Ser Ile Glu Arg Leu
        195                 200                 205

Leu Glu Met Glu Ser Leu Val Ala Asp Thr Ser Glu Glu Cys Gln Phe
    210                 215                 220

Leu Arg Val Gly Pro Asp Ser Asn Val Pro Pro Lys Phe Arg Ala Pro
225                 230                 235                 240

Val Ser Ser Leu Cys Gln Ile Gly Asn Lys Gln Ile Ala Ala Leu Val
```

-continued

```
                     245                 250                 255
Val Trp Ala Arg Asp Ile Pro His Phe Gly Gln Leu Glu Met Glu Asp
            260                 265                 270
Gln Val Leu Leu Ile Lys Ser Ala Trp Asn Glu Leu Leu Leu Phe Ala
        275                 280                 285
Ile Ala Trp Arg Ser Met Glu Phe Leu Thr Asp Glu Arg Glu Asn Met
    290                 295                 300
Asp Gly Thr Arg Ser Ser Pro Pro Gln Leu Met Cys Leu Met Pro
305                 310                 315                 320
Gly Met Thr Leu His Arg Asn Ser Ala Leu Gln Ala Gly Val Gly Gln
                325                 330                 335
Ile Phe Asp Arg Val Leu Ser Glu Leu Ser Leu Lys Met Arg Ala Leu
            340                 345                 350
Arg Met Asp Gln Ala Glu Tyr Val Ala Leu Lys Ala Ile Ile Leu Leu
        355                 360                 365
Asn Pro Asp Val Lys Gly Leu Lys Asn Arg Gln Glu Val Glu Val Leu
    370                 375                 380
Arg Glu Lys Met Tyr Ser Cys Leu Asp Glu Tyr Cys Arg Arg Ser Arg
385                 390                 395                 400
Gly Thr Glu Glu Gly Arg Phe Ala Ser Leu Leu Leu Arg Leu Pro Ala
                405                 410                 415
Leu Arg Ser Ile Ser Leu Lys Ser Phe Glu His Leu Phe Phe His
            420                 425                 430
Leu Val Ala Asp Ala Ser Ile Ala Ala Tyr Ile Arg Asp Ala Leu Arg
        435                 440                 445
Thr His Ala Pro Pro Ile Asp Ala Ser Ala Met Leu
    450                 455                 460

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence:
      oligonucleotide primer
<220> FEATURE:
<221> NAME/KEY: unsure
<222> LOCATION: (1)..(25)
<223> OTHER INFORMATION: n= a or g or c or t

<400> SEQUENCE: 5
cggaattcgg ntaycaytay aaygc                                    25

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 6
cctcgggacs acttcgtgaa tcc                                      23

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence:
      oligonucleotide primer
```

-continued

```
<400> SEQUENCE: 7
tgtgarggct gcaarggstt ctt                                               23

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 8
tgtgarggct gcaarggstt ctt                                               23
```

ECDYSONE RECEPTORS AND METHODS FOR THEIR USE

CROSS-REFERENCE TO RELATED APPLICATION

This application claims the benefit of U.S. Provisional Application No. 60/099,793, filed Sep. 10, 1998.

FIELD OF THE INVENTION

The field of the invention is inducible gene expression systems wherein expression is controlled by a novel ecdysone receptor or its derivatives. The field particularly relates to the isolation and characterization of nucleic acid and polypeptides for a novel ecdysone receptor. The nucleic acid and polypeptides are useful in novel gene expression systems inducible with ecdysone or derivative receptor agonists.

BACKGROUND OF THE INVENTION

The steroid hormone 20-hydroxyecdysone, also known as β-ecdysone, controls timing of development in many insects. Ecdysone triggers coordinate changes in tissue development that results in metamorphosis. See generally, Kollman (ed.) *Ecdysone: From Chemistry to Mode of Action*, Thieme Medical Pub., NY (1989), which is incorporated herein by reference. The generic term "ecdysone" is frequently used as an abbreviation for 20-hydroxyecdysone.

The Ecdysone receptor (EcR) polypeptide comprises a ligand-binding domain, a DNA-binding domain, and a transactivating domain. The receptor binds to 20-hydroxyecdysone and transactivates gene expression of a target gene in the nucleus.

The ligand-binding domain of the receptor polypeptide provides the means by which the 5' regulatory region of the target gene is activated in response to the hormone. Other chemicals, such as the non-steroidal ecdysone agonist RH5849 (Wing, *Science* 241:467–469 (1988)), will also act as a chemical ligand for the ligand-binding domain of EcR.

The DNA-binding domain comprises a sequence of amino acids that binds noncovalently to a response element, a specific nucleotide sequence in a target gene. A response element is located in the 5' regulatory region of a target gene that is activated by the hormone.

The transactivation domain comprises one or more amino acid sequences acting as subdomains to affect the operation of transcription factors during pre-initiation and assembly at the TATA box. The effect of the transactivation domain is to allow repeated transcription initiation events leading to greater levels of gene expression from the target gene. Binding of the ligand causes a conformational change in the receptor polypeptide and allows the transactivation domain to affect transcription of the coding sequence in the target gene, resulting in production of the target polypeptide.

The EcR in Drosophila exists in three isoforms, each with an independent biological function. All share the same heterodimeric partner, Ultraspiracle (USP). USP is most homologous to the retinoic acid receptor α, also capable of forming heterodimers with EcR (Thomas et al. *Nature* 362:471–475 (1993)). While each of the isoforms independently interacts with ecdysone, the addition of USP greatly enhances the affinity of the complex for binding to ecdysone response elements (EcRE) found in the promoters of genes. Ultraspiracle has been isolated and cloned and its ligand-binding domain identified (Henrich et al., *Nucleic Acids Research* 18:4143–4148 (1990)). See WO 94/01558.

Without bound ligand, the EcR/USP heteroduplex interacts weakly with the EcRE, inhibiting transcription. Binding of ecdysone or other ligand by the EcR/USP complex enhances its affinity for the EcRE, with the conformational changes in the complex functioning to facilitate transcription. The ecdysone heteromeric receptor complex binds the DNA with a high affinity and acts as a potent promoter of DNA transcriptional activation, with transient transcriptional inducibility facilitated by the presence of the ecdysone ligand.

It is often desirable to control the onset and extent of gene expression. The ability to selectively induce the expression of specific genes allows for the manipulation of development and function not only at the cellular but also at the system and organismal level. Thus, ecdysone receptor/Ultraspiracle provides a means of regulating gene expression. It provides for regulation using a chemical that may be extrinsically applied in order to trigger gene activation.

U.S. Pat. No. 4,981,784 discusses novel retinoic acid receptors encoding chimeric receptor proteins. The chimeras are constructed by exchanging functional domains between glucocorticoid, mineral corticoid, estrogen-related, thyroid, and retinoic acid receptors.

U.S. Pat. No. 5,310,662 discusses hormone and hormone-like receptors in which the transactivation domains are modified in terms of position or copy number, the receptors having increased transactivation properties.

U.S. Pat. No. 4,833,080 is directed to the regulation of eukaryotic gene expression controlled by prokaryotic peptides recognizing specific sequences in the gene and either activating or repressing transcription.

U.S. Pat. No. 5,554,510 is directed to regulating gene expression by providing a pair of unlike proteins, with unlike DNA-binding domains, which will form a heterodimer, bind to asymmetric DNA binding sites, and depress or increase gene expression.

U.S. Pat. No. 5,217,867 is directed to hormone and hormone-like receptors in which changes in position or copy number of the transactivation domain provides increased transactivation.

U.S. Pat. No. 5,571,696 is directed to members of the steroid/thyroid superfamily of receptors, DNA encoding these receptors, and methods for expressing them in host cells.

WO 90/11273 is directed to steroid/thyroid hormone receptor DNA-binding domain compositions that determine target site specificity, and methods for converting the target site specificity of one receptor into the target site specificity of another.

U.S. Pat. No. 5,298,429 is directed to bioassays for determining whether a compound is a hormone receptor agonist or antagonist, the assay involving a DNA sequence encoding a hormone response element operatively linked to a reporter gene.

U.S. Pat. No. 5,071,773 discusses hormone receptor bioassays useful to determine whether a protein, suspected of being a hormone receptor, has transcription-activating properties, and evaluating whether compounds are functional ligands for receptor proteins.

WO 93/21334 relates to chemically-inducible plant gene expression cassettes in plant cells transformed with the cassettes. An inducible promoter is operatively linked to a target gene, the inducible promoter being activated by a regulator protein also expressed in the cell. In the presence of an effective exogenous inducer, the activator protein induces expression of the target gene.

WO 93/23431 is directed to mutant steroid hormone receptors and methods for using these as a molecular switch in gene therapy.

WO 94/01558 is directed to various members of the steroid/thyroid superfamily of receptors that can interact with the insect-derived Ultraspiracle receptor to form multimeric species.

WO 92/16546 is directed to DNA segments that are response elements for ligands for several members of the steroid/thyroid superfamily of receptors. Response elements in combination with a functional promoter and gene provide recombinant vectors containing a gene responsive to ligands for members of the steroid/thyroid superfamily of receptors.

WO 93/11235 is directed to the interaction of various members of the steroid/thyroid superfamily of receptors to form multimers of more than one receptor. This modulates the ability of a first receptor to transactivate the transcription of genes maintained under the hormone expression control in the presence of the cognate ligand for the first receptor.

U.S. Pat. No. 5,534,418 is directed to methods for controlled production of recombinant proteins in cells. Transcription of the gene encoding the protein is maintained under the control of a transcription control element that is activated by a ligand receptor complex. The complex is formed when a ligand (a hormone or analog of a hormone) is complexed with a receptor (which is a hormone receptor or functional analog).

WO 91/13167 is directed to the isolation of insect DNA sequences having the characteristics of insect steroid receptors.

WO 96/27673 discusses recombinant inducible gene expression systems involving the ecdysone receptor. Chimeric receptors are made in which either the ligand-binding domain, the transactivator domain, or the DNA-binding domain are heterologous in the recombinant receptor. The construct is used to activate a target gene in a plant cell.

U.S. Pat. No. 5,514,578 discloses polynucleotide sequences that encode ecdysone receptors and their expression in host cells.

WO 96/37609 is directed to an ecdysone receptor protein capable of acting as a gene switch responsive to a chemical inducer, enabling external control of a gene.

WO 93/03162 is directed to a method for inducing gene expression by contacting an ecdysteroid with an ecdysteroid receptor polypeptide in a mammalian cell. The cell contains a DNA binding sequence for the receptor.

U.S. Pat. No. 5,880,333 is directed to a method for controlling gene expression in a plant through the expression of class II steroid and thyroid hormone superfamily of nuclear hormones. Chimeric receptors are generated in which either the ligand-binding domain, the DNA binding domain or the transactivator domain are heterologous in the recombinant receptor. The chimeric receptors are used to regulate expression of target sequences.

U.S. Pat. No. 5,432,068 is directed to a method for controllably rendering plants male fertile by using an inducible promoter to regulate expression of a gene critical to male fertilization such that when the gene is "off," the plant is sterile; however, when the promoter is induced, the plant becomes fertile. In particular, it is directed to a method whereby a gene affecting flavonol production in a plant is controlled in a manner rendering the plant conditionally male fertile. Related U.S. Pat. No. 5,478,369 discloses nucleotide and amino acid sequences mediating male fertility in plants.

U.S. Pat. Nos. 5,824,524 and 5,850,014 also relate to control of plant fertility by providing a constitutively sterile plant, wherein fertility may be induced using male fertility MS45 DNA molecules or genes impacting flavonone production.

U.S. Pat. No. 5,859,341 is directed to a method for providing heritable, externally controllable male fertility through selective induction of microsporogenesis.

While some ecdysone receptors are known, there is a need for the isolation and use, especially in plants, of additional receptors. The invention is thus directed to novel ecdysone receptors. While the invention may have an impact on the furtherance of the understanding of insect physiology, the potential use of the receptor peptides in the control of gene expression, particularly in plants, is of primary interest.

SUMMARY OF THE INVENTION

Accordingly, the invention is directed to a novel protein from the insect genus Pyrilidue, the protein being responsive to ecdysone.

The invention is particularly directed to the protein from the species Ostrinia, and especially *Ostrinia nubilalis*.

The invention encompasses a novel protein that acts as an ecdysone receptor in these species.

The invention is specifically directed to a protein comprising the amino acid sequence in SEQ ID NO 2.

The invention also encompasses a further novel protein from a Pyrilidae species that binds with the novel ecdysone receptor to form a heterodimer. This protein can be designated the "LIltraspiracle" protein. Thus the invention specifically is directed to a protein comprising the amino acid sequence in SEQ ID NO 3.

The proteins are useful, alone or in combination, for activating a target gene in response to a chemical inducer such as ecdysone, an ecdysone derivative, or an ecdysone mimic.

The invention is also directed to a chimeric receptor protein in which one or more of the ligand binding, DNA binding, or transactivation domains in the novel ecdysone receptor are obtained from a source heterologous with respect to the other domains present in the chimeric receptor protein. Chimeric receptor proteins provide flexibility in the choice of ligand and choice of target sequence to be activated, and thus allow controlled gene expression in a cell or in an organism.

The choice of the heterologous source will depend upon the desired specificity and effectiveness level for transactivation, ligand binding, or DNA binding. Accordingly, the chimeric receptor molecules confer the advantage of: (1) maximizing transactivation by using a transactivator domain stronger than the native domain and allowing transactivation in a specific host cell by using a transactivator that is compatible with a particular host cell; (2) providing induction by a selected chemical ligand by replacing the ligand binding site with a binding site for another ligand; and (3) use of specific response elements by replacing the native DNA binding site with a site that recognizes different response elements (i.e. other than EcRE).

The invention is also directed to an isolated nucleotide sequence encoding these proteins. In particular, the invention is directed to the nucleotide sequence shown in SEQ ID NO: 1 (ecdysone receptor) and SEQ ID NO: 3 (Ultraspiracle).

The invention also encompasses expression vectors comprising the nucleotide sequences.

The invention also encompasses cells containing the expression vectors and/or expressing the nucleotide sequences.

The invention also provides methods for screening for ligands that bind to the proteins described herein.

In preferred embodiments of the invention, the cell in which the receptor is expressed and the target gene activated is a plant cell.

The invention also provides methods to regulate plant fertility.

DETAILED DESCRIPTION OF THE INVENTION

The invention is directed to novel proteins that are responsive to ecdysone, being derived from the genus Pyrilidae and particularly from the species Ostrinia, specifically *Ostrinia nubilalis*. Compositions of the invention include a novel Ecdysone receptor (EcR) and the Ultraspiracle (USP) receptor. Both of these receptors have homology to members of the steroid/hormone receptor superfamily and are involved in activating transcription of a target gene in response to a chemical inducer. In particular, the present invention provides for isolated nucleic acid molecules comprising nucleotide sequences encoding the amino acid sequences shown in SEQ ID NOS: 2 or 4. Further provided are polypeptides having an amino acid sequence encoded by a nucleic acid molecule described herein, for example those set forth in SEQ ID NOS: 1 or 3 and fragments and variants thereof.

The invention encompasses isolated or substantially purified nucleic acid or protein compositions. An "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A protein that is substantially free of cellular material includes preparations of protein having less than about 30%, 20%, 10%, 5%, (by dry weight) of contaminating protein. When the protein of the invention or biologically active portion thereof is recombinantly produced, preferably culture medium represents less than about 30%, 20%, 10%, or 5% (by dry weight) of chemical precursors or non-protein-of-interest chemicals.

It is understood, however, that there are embodiments in which preparations that do not contain the substantially pure protein may also be useful. Thus, less pure preparations can be useful where the contaminating material does not interfere with the specific desired use of the peptide.

Fragments and variants of the disclosed nucleotide sequences and proteins encoded thereby are also encompassed by the present invention. By "fragment" is intended a portion of the nucleotide sequence or a portion of the amino acid sequence and hence protein encoded thereby. Fragments of a nucleotide sequence may encode protein fragments that retain one or more of the functional biological activities of the native protein. Accordingly, a fragment of a nucleotide sequence may retain a functional ligand-binding domain, transactivation domain or DNA binding domain.

A fragment of an Ultraspiracle or Ecdysone receptor nucleotide sequence that encodes a biologically active portion of an Ultraspiracle or Ecdysone receptor of the invention will encode at least 15, 25, 30, 50, 100, 150, 200, 250, 300, 350, 400, 450 contiguous amino acids, or up to the total number of amino acids present in a full-length receptor of the invention (for example, 546 or 460 amino acids for SEQ ID NOS: 2 and 4, respectively). Fragments of a nucleotide sequence encoding an Ultraspiracle or Ecdysone receptor that are useful as hybridization probes for PCR primers generally need not encode a biologically active portion of an Ultraspiracle or Ecdysone receptor.

Thus, a fragment of a nucleotide sequence encoding an Ultraspiracle or Ecdysone receptor may encode a biologically active portion of a receptor, or it may be a fragment that can be used as a hybridization probe or PCR primer using methods disclosed below. A biologically active portion of an Ultraspiracle or Ecdysone receptor can be prepared by isolating a portion of one of the nucleotide sequences encoding a receptor of the invention, expressing the encoded portion of the receptor (e.g., by recombinant expression in vitro), and assessing the activity of the encoded portion of the receptor. Nucleic acid molecules that are fragments of an Ultraspiracle or Ecdysone receptor nucleotide sequence comprise at least 16, 20, 50, 75, 100, 150, 200, 250, 300, 350, 400, 450, 500, 550, 600, 650, 700, 800, 900, 1,000, 1,100, 1,200, 1,300, or 1,400, 1,500, 1,600, 1,700, 1,800 nucleotides, or up to the number of nucleotides present in a full-length Ultraspiracle or Ecdysone receptor nucleotide sequence disclosed herein (for example, 2,126 and 1,837 nucleotides for SEQ ID NOS: 1 and 2, respectively).

Also encompassed in these fragments are nonfunctional fragments that are useful, among other things, for diagnostic assays. Accordingly, a nonfunctional ligand binding domain fragment can have use as a binding antagonist that will compete with a functional ligand binding domain. Such a fragment can, for example, bind a ligand but be unable to confer the conformational change necessary for DNA binding. Similarly, a nonfunctional DNA binding domain may bind to DNA in such a manner that it prevents transactivation and consequent gene expression, while also preventing DNA binding by a functional DNA binding domain. Similarly, a nonfunctional transactivation domain may interfere with transcription induced by host cell components.

Alternatively, fragments of a nucleotide sequence that are useful as hybridization probes generally do not encode fragment proteins retaining biological activity. Thus, fragments of a nucleotide sequence may range from at least about 20 nucleotides, about 50 nucleotides, about 100 nucleotides, and up to the full-length nucleotide sequence encoding the proteins of the invention.

By "variants" is intended substantially similar sequences. For nucleotide sequences, conservative variants include those sequences that, because of the degeneracy of the genetic code, encode the amino acid sequence of one of the Ultraspiracle or Ecdysone receptor polypeptides of the invention. Naturally occurring allelic variants such as these can be identified with the use of well-known molecular biology techniques, as, for example, with polymerase chain reaction (PCR) and hybridization techniques as outlined below. Variant nucleotide sequences also include synthetically derived nucleotide sequences, such as those generated, for example, by using site-directed mutagenesis but which still encode a Ecdysone or Ultraspirical receptor of the invention. Generally, nucleotide sequence variants of the invention will have at least 40%, 50%, 60%, 70%, generally, 80%, preferably 85%, 90%, up to 95%, 98% sequence identity to its respective native nucleotide sequence.

By "variant" protein is intended a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Such variants may result from, for example, genetic polymorphism or from human manipulation.

The proteins of the invention may be altered in various ways including amino acid substitutions, deletions, truncations, and insertions. Methods for such manipulations are generally known in the art. For example, amino acid sequence variants of the Ultraspiracle or Ecdysone receptor proteins can be prepared by mutations in the DNA. Methods for mutagenesis and nucleotide sequence alterations are well known in the art. See, for example, Kunkel (1985) *Proc. Natl. Acad. Sci. USA* 82:488–492; Kunkel et al. (1987) *Methods in Enzymol.* 154:367–382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be preferred.

Thus, the genes and nucleotide sequences of the invention include both the naturally occurring sequences as well as mutant forms. Likewise, the proteins of the invention encompass both naturally occurring proteins as well as variations and modified forms thereof Such variants will continue to retain a functional ligand-binding domain, trans-activation domain or DNA binding domain. Obviously, the mutations that will be made in the DNA encoding the variant must not place the sequence out of reading frame and preferably will not create complementary regions that could produce secondary mRNA structure. See, EP Patent Application Publication No. 75,444.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays. That is, the activity can evaluated by the ability of the receptor to bind ligand, interact with DNA, or activate transcription.

Variant nucleotide sequences and proteins also encompass sequences and proteins derived from a mutagenic and recombinogenic procedure such as DNA ashuffling. With such a procedure, one or more different Ultraspiracle or Ecdysone receptor coding sequences can be manipulated to create a new receptor possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the Ecdysone or Ultraspirical receptor genes of the invention and other known steroid/hormone receptors or gene activator proteins to obtain a new gene coding for a protein with an improved property of interest, such as an increased $K_m$ in the case of an enzyme. Strategies for such DNA shuffling are known in the art. See, for example, Stemmer (1994) *Proc. Natl. Acad. Sci. USA* 91:10747–10751; Stemmer (1994) *Nature* 370:389–391; Crameri et al. (1997) *Nature Biotech.* 15:436–438; Moore et al. (1997) *J. Mol. Biol.* 272:336–347; Zhang et al. (1997) *Proc. Natl. Acad Sci. USA* 94:4504–4509; Crameri et al. (1998) *Nature* 391:288–291; and U.S. Pat. Nos. 5,605,793 and 5,837,458.

In addition, protein variants encompassed by the present invention include those that contain mutations that either enhance or decrease one or more domain functions. For example, in the ligand binding domain, a mutation may be introduced that increases the sensitivity of the domain to a specific ligand so that gene expression can be increased. Alternatively, it may be desired to introduce a mutation that reduces sensitivity of the domain to an undesirable ligand that may compete with a desired ligand. Similarly, mutations may be introduced into the DNA binding and transactivation domains that increase or reduce the finctionality of these domains. As an alternative to the introduction of mutations, increase in function may be provided by increasing the copy number of these domains. Thus, the invention also encompasses proteins in which one or more of the domains is provided in more than one copy.

The nucleotide sequences of the invention can be used to isolate corresponding sequences from other organisms. In this manner, methods such as PCR, hybridization, and the like can be used to identify such sequences based on their sequence homology to the sequences set forth herein. Sequences isolated based on their sequence identity to the entire receptor sequences set forth herein or to fragments thereof are encompassed by the present invention.

In a PCR approach, oligonucleotide primers can be designed for use in PCR reactions to amplify corresponding DNA sequences from cDNA or genomic DNA extracted from any organism of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the receptor sequences of the invention. Methods for preparation of probes for hybridization and for construction of cDNA and genomic libraries are generally known in the art and are disclosed in Sambrook etal. (1989) *Molecular Cloning: A Laboratory Manual* (2d ed., Cold Spring Harbor Laboratory Press, Plainview, N.Y.).

For example, the entire sequence of Ultraspiracle or Ecdysone receptor disclosed herein, or one or more portions thereof, may be used as a probe capable of specifically hybridizing to corresponding Ultraspiracle or Ecdysone receptor sequences and messenger RNAs. To achieve specific hybridization under a variety of conditions, such probes include sequences that are unique among Ultraspiracle or Ecdysone receptor sequences and are preferably at least about 10 nucleotides in length, and most preferably at least about 20 nucleotides in length. Such probes may be used to amplify corresponding Ecdysone receptor or Ultraspirical sequences from a chosen organism by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 MNaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267–284: $T_m=81.5°$ C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point $(T_m)$ for the specific sequence and its complement at a defined ionic strength and pH. However, severely stringent conditions can utilize a hybridization and/or wash at 1, 2, 3, or 4° C. lower than the thermal melting point $(T_m)$; moderately stringent conditions can utilize a hybridization and/or wash at 6, 7, 8, 9, or 10° C. lower than the thermal melting point $(T_m)$; low stringency conditions can utilize a hybridization and/or wash at 11, 12, 13, 14, 15, or 20° C. lower than the thermal melting point $(T_m)$. Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, N.Y.); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

Thus, isolated sequences that encode for an Ecdysone receptor or Ultraspirical protein and which hybridize to the Ecdysone receptor or Ultraspirical sequences disclosed herein, or to fragments thereof, are encompassed by the present invention. Such sequences will be at least 40% to 50% homologous, about 60% to 70% homologous, and even about 80%, 85%, 90%/0, 95% to 98% homologous or more with the disclosed sequences. That is, the sequence similarity of sequences may range, sharing at least about 40% to 50%, about 60% to 70%, and even about 80%, 85%, 90%, 95% to 98% sequence similarity.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Optimal alignment of sequences for comparison may be conducted by the local homology algorithm of Smith et al. (1981) *Adv. Appl Math.* 2:482; by the homology alignment algorithm of Needleman et al. (1970) *J. Mol. Biol.* 48:443; by the search for similarity method of Pearson et al. (1988) *Proc. Natl. Acad. Sci.* 85:2444; by computerized implementations of these algorithms, including, but not limited to: CLUSTAL in the PC/Gene program by Intelligenetics, Mountain View, Calif.; GAP, BESTFIT, BLAST, FASTA, and TFASTA in the Wisconsin Genetics Software Package, Genetics Computer Group (GCG), 575 Science Drive, Madison, Wis., USA; the CLUSTAL program is well described by Higgins et al. (1988) *Gene* 73:237–244 (1988); Higgins et al. (1989) *CABIOS* 5:151–153; Corpet et al. (1988) *Nucleic Acids Res.* 16:10881–90; Huang et al. (1992) *Computer Applications in the Biosciences* 8:155–65, and Person et al. (1994) *Meth. Mol. Biol.* 24:307–331; preferred computer alignment methods also include the BLASTP, BLASTN, and BLASTX algorithms (see Altschul et al. (1990) *J. Mol. Biol.* 215:403–410). Alignment is also often performed by inspection and manual alignment. Sequence alignments are performed using the default parameters of the above mentioned programs.

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70% sequence identity, preferably at least 80%, more preferably at least 90%, and most preferably at least 95%, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 60%, more preferably at least 70%, 80%, 90%, and most preferably at least 95%.

Another indication that nucleotide sequences are substantially identical is if two molecules hybridize to each other under stringent conditions. Generally, stringent conditions are selected to be about 5° C. lower than the thermal melting point $(T_m)$ for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70% sequence identity to a reference sequence, preferably 80%, more preferably 85%, most preferably at least 90% or 95% sequence identity to the reference sequence over a specified comparison window. Preferably, optimal alignment is conducted using the homology alignment algorithm of Needleman et al. (1970) *J. Mol. Biol.* 48:443. An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides that are "substantially similar" share sequences as noted above except that residue positions that are not identical may differ by conservative amino acid changes.

The protein can be purified from cells that naturally express it, purified from cells that have been altered to express it (i.e. recombinant) or synthesized using protein synthesis techniques that are well known in the art. In a preferred embodiment, the protein is produced by recombinant DNA methods. In such methods a nucleic acid molecule encoding the protein is cloned into an expression vector as described more fully herein and expressed in an appropriate host cell according to known methods in the art. The protein is then isolated from cells using protein purification techniques well known to those of ordinary skill in the art. Alternatively, the protein or fragment can be synthesized using peptide synthesis methods well known to those of ordinary skill in the art.

The invention also encompasses chimeric proteins in which a heterologous protein, having an amino acid sequence that is not substantially homologous to the protein of the invention, forms a fusion protein with a protein, or fragment or variant thereof, of the invention. These proteins may or may not be operatively linked. An example of operative linkage is fusion in-frame so that a single protein is produced upon translation. Such fusion proteins can, for example, facilitate the purification of a recombinant protein. In another embodiment, the fusion protein may contain a heterologous signal sequence at the N-terminus facilitating its secretion from specific host cells. The expression and secretion of the protein can thereby be increased by use of the heterologous signal sequence.

The invention is particularly directed to proteins in which one or more domains in the protein described herein are operatively linked to heterologous domains having homologous functions. Thus, the ligand binding domain can be replaced with a ligand binding domain for other ligands. Thereby, the control of gene expression is based on a ligand other than ecdysone but gene expression in the nucleus depends upon ecdysone response elements. Alternatively, the native ligand binding domain may be retained while the DNA binding domain is replaced with a binding domain that recognizes a heterologous response element. Thus, while the sequence of events for gene expression is initiated by ecdysone or other appropriate ligand, ultimate gene expression depends upon the presence of a response element corresponding to the heterologous DNA binding sequence. Furthermore, the transactivation region can be replaced depending upon the cell type in which gene expression is desired. Thus, in order to recruit transcription factors in a specific cell type, a transactivation region compatible with that cell type can replace the native transactivation domain.

Ligand binding domains may be obtained from members of the class II receptor proteins of the steroid/thyroid hormone superfamily of nuclear receptors, which include, but are not limited to, retinoic acid receptor, vitamin D receptor, and thyroid hormone receptor.

Transactivation domains may also be obtained from members of the class II receptor proteins of the steroid/thyroid hormone superfamily of nuclear receptors, which include, but are not limited to, retinoic acid receptor, vitamin D receptor, and thyroid hormone receptor. Alternatively, the transactivation domain may be obtained from other transcriptional activators including, but not limited to VP 16 from herpes simplex, maize Cl, and GAL4.

DNA binding domains may be also be obtained from members of the class II receptor proteins of the steroid/thyroid hormone superfamily of nuclear receptors, which include, but are not limited to, retinoic acid receptor, vitamin D receptor, and thyroid hormone receptor. Alternatively, the DNA binding domain may be obtained from other transcriptional activators including, but not limited to LexA, and GAL4.

As used herein, the term "recombinant" refers to in vitro cleavage and religation of nucleotide sequences as well as cleavage and ligation in the cell or in the organism that results from, for example, integration of exogenous sequences into the cellular endogenous sequences, as by homologous recombination.

The nucleic acid can be purified from cells that naturally express it, for example, a cell in which the sequence is amplified, or from cells in which it has been exogenously introduced, i.e., a recombinant cell. Alternatively, nucleic acid can be synthesized using synthesis techniques well known in the art. Thus, nucleotides encoding the proteins described herein can be cloned into expression vectors, amplified, and expressed in an appropriate host cell.

The invention also encompasses nucleotide sequences that provide fusion proteins in which a heterologous protein, having an amino acid sequence not substantially homologous to the proteins of the invention, forms a fusion protein with the proteins of the invention. These nucleotide sequences may or may not provide for operative linkage.

The invention is particularly directed to nucleotide sequences encoding proteins in which one or more domains in the protein is operatively linked to a heterologous domain having a homologous function. Thus, the ligand binding domain can be replaced with a ligand binding domain for another ligand. Alternatively, the native ligand binding domain can be retained while the DNA binding domain is replaced with a binding domain recognizing a heterologous response element. Finally, the transactivation region can also be replaced by a adesired transactivation region.

The invention further encompasses cells containing, in addition to the receptor expression vectors (i.e. the ecdysone receptor, Ultraspiracle, or chimeric derivatives), nucleotide sequences that serve as a target for proteins expressed from the receptor expression vectors. The target comprises a regulatory region operably linked to a nucleotide sequence encoding a target polypeptide whose expression is controlled by addition of a ligand and consequent activation of the receptor protein. The regulatory region contains a core promoter sequence, a sequence that allows the initiation of transcription, and response elements for binding receptor.

Accordingly, the expression of any desired coding sequence can be desirably controlled as long as the promoter controlling the transcription of the coding sequence is designed to contain a response element complementary to the DNA binding domain of the receptor polynucleotide. The level of expression can be controlled by the choice of transactivator. The induction of the expression can be controlled by the ligand choice.

Accordingly, the invention is further directed to methods for controlling the expression of a specific gene and the production of a gene product by providing a chemical ligand that interacts with the proteins described herein.

Either the ecdysone receptor or the USP protein or a combination thereof (as a heterodimer) can be used. In embodiments in which the ecdysone receptor is used alone, one or more mutations may be made in one or more of the domains in order to achieve a desired level of gene activation.

The system can consist of two or more expression cassettes used to transform a host cell. The first expression cassette could contain the sequences for the EcR and/or USP proteins or their equivalents. Transcription of these genes can be placed under the control of a promoter, such as a constitutive or inducible promoter or a tissue—or cell cycle-preferred promoter. The second expression cassette contains a target sequence.

The target sequence encodes a protein of interest for which ligand-inducible expression is desired. Such target sequences could include, but are not limited to, genes encoding insecticide or herbicide resistance, nutritional factors, growth inducers, and genes required for fertility. Such a target sequence follows an ecdysone or other appropriate response element contained within its promoter region.

In one embodiment, the EcR/USP heterodimer expressed in the transformed cell preferentially binds the ecdysone response element upstream of the target sequence. When the ligand for the heterodimer is introduced into the host cell the EcR/USP/ligand complex acts to facilitate gene expression. Specific recognition sequences comprising a ligand response element for EcR/USP recognition are well-known in the art and may be effectively engineered into the promoter region of a target gene through commonly employed molecular biological techniques. See, for example, Crispi, S., *J. Mol. Biol.* 275(4):561–574 (1998); Antoniewski, C., *Mol. Cell.*

Biol. (6):2977–2986 (1996); Jones, C., *Insect Biochem. Mol. Biol.* (9): 875–882 (1994); Antoniewski, C., *Mol. Gen. Genet.* 249(5):545–556 (1995 Dec 15, 1995 ); Antoniewski, C., *Mol. Cell. Biol.* (7):4465–4474 (1994); Antoniewski, C., *Insect Biochem. Mol. Biol.* (1): 105–114 (1993).

A preferred embodiment of this invention thus embodies the response element recognized by either the EcR/USP complex or a modified derivative thereof, including EcR or USP alone in a chimeric construct, which is engineered into the promoter of a target gene. This construct may then be employed to co-transform a host cell along with an expression cassette containing the EcR and/or USP nucleic acid sequences or a derivative thereof. In the presence of the ligand recognized by the EcR receptor polypeptide, the target gene is selectively induced. Induction in this fashion may be ligand concentration dependent, with increasing concentrations of the ligand resulting in higher levels of gene expression. Thus, by linking a ligand responsive element to a peptide encoding segment, a protein expression system may be developed in which protein production is regulated by the administration of a ligand.

In another embodiment, expression of EcR alone or a chimeric derivative thereof, regulates transcription of the target sequences. In this embodiment a response element recognized by EcR or a chimeric derivative thereof is engineered into the transcriptional regulatory region of the target sequence. Addition of ligand, results in the activation of EcR and the expression of the target sequences.

The term "nucleic acid" refers to all forms of DNA such as cDNA or genomic DNA and RNA such as mRNA, as well as analogs of the DNA or RNA generated using nucleotide analogs. The nucleic acid molecules can be single stranded or double stranded. Strands can include the coding or non-coding strand.

The proteins or other component polypeptides described herein may be used alone or in combination with other proteins or agents to facilitate gene expression. It is recognized in the art that the components of the ecdysonal binding system may be substituted with other components of related hormone response elements to achieve substantially similar effects.

The nucleotide sequences encoding the proteins of the invention can be manipulated and used to express the protein in a variety of hosts including microorganisms and plants. It is recognized that the proteins and DNA sequences of the invention may be used alone or in combination with other proteins.

The proteins of the invention can be used in expression cassettes for expression in any host of interest. Such expression cassettes will comprise a transcriptional initiation region linked to the gene encoding the protein of interest. Such an expression cassette can be provided with a plurality of restriction sites for insertion of the gene of interest to be under the transcriptional regulation of the regulatory regions. The expression cassette may additionally contain selectable marker genes suitable for the particular host organism to be used.

The transcriptional initiation region, the promoter, may be native or analogous or foreign or heterologous to the plant host. Additionally, the promoter may be the natural sequence or alternatively a synthetic sequence. By "foreign" is intended that the transcriptional initiation region is not found in the native plant into which the transcriptional initiation region is introduced. As used herein, a chimeric gene comprises a coding sequence operably linked to a transcription initiation region that is heterologous to the coding sequence.

Any promoter or promoter element capable of driving expression of a coding sequence can be utilized. For instance, constitutive promoters include, for example, the core promoter of the Rsyn7 (copending U.S. application Ser. No. 08/661,601); the core CaMV 35S promoter (Odell et al. (1985) *Nature* 313:810–812); rice actin (McElroy et al. (1990) *Plant Cell* 2:163–171); ubiquitin (Christensen et al. (1989) *Plant Mol. Biol.* 12:619–632 and Christensen et al. (1992) *Plant Mol. Biol.* 18:675–689); pEMU (Last et al. (1991) *Theor. Appl. Genet.* 81:581–588); MAS (Velten et al. (1984) *EMBO J.* 3:2723–2730); ALS promoter (U.S. application Ser. No. 08/409,297), and the like. Other constitutive promoters include, for example, U.S. Pat. Nos. 5,608,149; 5,608,144; 5,604,121; 5,569,597; 5,466,785; 5,399,680; 5,268,463; and 5,608,142.

Alternatively, tissue-preferred promoters can be utilized to target enhanced EcR or USP expression within a particular plant tissue. Tissue-preferred promoters include Yamamoto et al. (1997) *Plant J.* 12(2)255–265; Kawamata et al. (1997) *Plant Cell Physiol.* 38(7):792–803; Hansen et al. (1997) *Mol. Gen Genet.* 254(3):337–343; Russell et al. (1997) *Transgenic Res.* 6(2):157–168; Rinehart et al. (1996) *Plant Physiol.* 112(3): 1331–1341; Van Camp et al. (1996) *Plant Physiol.* 112(2):525–535; Canevascini et al. (1996) *Plant Physiol.* 112(2):513–524; Yamamoto et al. (1994) *Plant Cell Physiol.* 35(5):773–778; Lam (1994) *Results Probl. Cell Differ.* 20:181–196; Orozco et al. (1993) *Plant Mol. Biol.* 23(6):1129–1138; Matsuoka et al. (1993) *Proc Natl. Acad Sci. USA* 90(20):9586–9590; and Guevara-Garcia et al. (1993) *Plant J.* 4(3):495–505. Such promoters can be modified, if necessary, for weak expression.

Of particular interest are promoters which direct expression in the reproductive organs of the plant. Such promoters include, but are not limited to, for example, anther, tapetal, pistil, and ovule-preferred promoters. Examples of anther-preferred promoters include ant32 and ant43D (U.S. patent application Ser. No. 07/908,242), anther (tapetal) promoter B6 (Huffman et al. (1993) *J. Cell. Biochem.* 17B: Abstract #D209) and promoter 5126 (U.S. Pat. No. 5,795,753). Other examples of anther-preferred promoters may also be found in U.S. patent application Ser. No. 5,470,359. A pistil-preferred promoter, includes for example, the modified S14 promoter (Dzelkalns et al. (1993) *Plant Cell* 5:855.

The transcriptional cassette will include in the 5'-3' direction, the orientation of transcription, a transcriptional initiation region, a translational initiation region, a DNA sequence of interest, a translational termination region, and a transcriptional termination region functional in plants. The termination region may be native with respect to the transcriptional initiation region, may be native with respect to the DNA sequence of interest, or may be derived from other sources. Convenient termination regions are available from the Ti-plasmid of *A. tumefaciens*, such as the octopine synthase and nopaline synthase termination regions. See also, Guerineau et al., (1991) *Mol. Gen. Genet.* 262:141–144; Proudfoot (1991) *Cell* 64:671–674; Sanfacon et al. (1991) *Genes Dev.* 5:141–149; Mogen et al. (1990) *Plant Cell* 2:1261–1272; Munroe et al. (1990) *Gene* 91:151–158; Ballas etal. 1989) *Nucleic Acids Res.* 17:7891–7903; Joshi etal. (1987) *Nucleic Acids Res.* 15:9627–9639.

Expression cassettes for the expression of co-transformed target genes will include a promoter region specific for response element binding in a position proper to promote expression of the target gene. Thus such a region will be included a proper distance upstream of the cloning site for the gene and in the proper orientation. Otherwise, expression cassettes for target genes may include all of the required elements previously discussed.

The nucleotide sequences encoding the proteins or polypeptides of the invention are particularly useful in the genetic manipulation of plants. In this manner, the genes of the invention are placed into expression cassettes for expression in the plant of interest. The cassette will include 5' and 3' regulatory sequences operably linked to the gene of interest. The cassette may additionally contain at least one additional gene to be cotransformed into the organism. Alternatively, other gene(s) of interest can be provided on other expression cassettes. Where appropriate, the gene(s) may be otherwise optimized for increased expression in the transformed plant. That is, the genes can be synthesized using plant preferred codons for improved expression. Methods are available in the art for synthesizing plant preferred genes. See, for example, U.S. Pat. Nos. 5,380,831, 5,436, 391, and Murray etal. (1989) Nucleic Acids Res. 17:477–498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences in the expression cassette construct. Such leader sequences can act to enhance translation. Translational leaders are known in the art and include: picornavirus leaders, for example, EMCV leader (Encephalomyocarditis 5' noncoding region) (Elroy-Stein, O., Fuerst, T. R., and Moss, B. (1989) *PNAS USA*, 86:6126–6130); potyvirus leaders, for example, TEV leader (Tobacco Etch Virus) (Allison et al. (1986); MDMV leader (Maize Dwarf Mosaic Virus); *Virology*, 154:9–20), and human immunoglobulin heavy-chain binding protein (BiP), (Macejak, D. G., and P. Sarnow (1991) *Nature*, 353:90–94; untranslated leader from the coat protein mRNA of alfalfa mosaic virus (AMV RNA 4), (Jobling, S. A., and Gehrke, L., (1987) *Nature*, 325:622–625; tobacco mosaic virus leader (TMV), (Gallie, D. R. et al. (1989) *Molecular Biology of RNA*, pages 237–256; and maize chlorotic mottle virus leader (MCMV) (Lommel, S. A. et al. (1991) *Virology*, 81:382–385). See also, Della-Cioppa et al. (1987) *Plant Physiology*, 84:965–968. Other methods known to enhance expression can also be utilized, for example, introns, and the like.

In preparing the expression cassette, the various DNA fragments may be manipulated, so as to provide for the DNA sequences in the proper orientation and, as appropriate, in the proper reading frame. Towards this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resection, ligation, PCR, or the like may be employed, where insertions, deletions or substitutions, e.g. transitions and transversions, may be involved.

The invention encompasses various ligands. The first non-steroidal ecdysteroid agonists, dibenzoyl hydrazines, typified by RH-5849 [1,2-dibenzoyl, 1-tert-butyl hydrazide], which is commercially available as an insecticide from Rohm and Haas, were described back in 1988. Another commercially available compound in this series is RH-5992 [tebufenozide, 3,5-dimethylbenzoic acid 1-1 (1,1-dimethylethyl)-2(4-ethylbenzoyl) hydrazide]. These compounds mimic 20-hydroxyecdysone (20E) in both *Manduca sexta* and *Drosophila melanogaster*. These compounds have the advantage that they have the potential to control insects using ecdysteroid agonists that are non-steroidal. Further examples of such dibenzoyl hydrazines are given in U.S. Pat. No. 5,117,057 to Rohm and Haas, and Oikawa et al., *Pestic. Sci.* 41:139–148 (1994). However, it will be appreciated that any inducer of the gene switch of the present invention, whether steroidal or non-steroidal, and which is currently or becomes available, may be used. A preferred ligand is methoxyfenozide.

| | |
|---|---|
| Chemical Abstract Name: | Benzoic Acid, 3-methoxy-2-methyl-2-(3,5-dimethylbenzoyl)-2-(1, 1 dimethylethyl) hydrazide |
| IUPAC Name: | N'-t-butyl-N'-(3, 5-dimethylbenzoyl)-3-methoxy-2-methylbenzohydrazide |
| Common Name: | methoxyfenozide |
| Trade Name: | INTREPID ™ Insecticide |
| CAS Number: | 161050-58-4 |
| Empirical Formula: | $C_{22}H_{28}N_2O_3$ |
| Molecular Weight: | 368.47 |

Analogs of ecdysone, such as Muristerone A, are also encompassed by the present invention.

The peptide products of the nucleotide sequences of the invention may also be used to elucidate other potential ligand analogs. The screening of diverse libraries of small molecules created by combinatorial synthetic methods may be used to identify compounds with binding affinity. One of skill in the art would be able to use the peptide sequences provided to develop sensitive assays to screen for both agonists and antagonists of ligand binding.

In constructing expression cassettes for the EcR or USP expression as well as for target gene expression, a variety of commonly recognized plasmids may be employed. One of skill in the art would recognize that competent cells could be transformed with expression cassettes that facilitate autonomous replication or integrate into the host cell chromosome. The EcR, USP and target gene could be included in a single cassette or multiple cassettes. Further it is envisioned by the inventors that the EcR or USP could be employed to regulate the expression of multiple target genes in a transformed host cell.

The EcR or USP peptide of the invention may also be combined with other members of the steroid/hormone receptor family. See, for example, Rowe, A. (1997) *Int. J. Biochem. Cell. Biol.*, (2): 275–278; Glass, C. (1996) *J. Endocrinol*, 150(3):349–357; Chambon, P. (1996) *FASEB J.*, 10(9): 940–954; Mangelsdorf, D. (1996) *Cell*, 83(6): 841–850. Members of the steroid/thyroid hormone receptor superfamily of DNA binding nuclear hormone receptor have been shown to react across species. Thus the substitution of trans retinoid acid, thyroid hormone, vitamin D or peroxisome proliferator-activated receptors for EcR could facilitate DNA interaction. Such chimeric proteins could provide an important reflection of the binding properties of the members of the superfamily. Such combinations could be further used to extend the range of applicability of these molecules in a wide range of systems or species that might not otherwise be amenable to native or relatively homologous proteins. Thus chimeric constructs could be substituted into systems in which a native construct would not be functional because of species specific constraints. Hybrid constructs may further exhibit desirable or unusual characteristics otherwise unavailable with the combinations of native proteins.

In another embodiment of the invention, methods are provided for screening for ligands that bind to the proteins described herein. Accordingly, both the proteins and relevant fragments thereof (for example, the ligand binding domain) can be used to screen for compounds that bind to the receptor and thus, induce gene expression. The assays may be cell-based or cell free assays which include the steps of exposing a ligand binding domain, either soluble or in association with a cell, to a candidate compound and either detecting the formation of a complex or detecting a biological event associated with gene expression caused by the activated receptor.

In other embodiments of the invention, it may be desirable to negatively control gene expression, particularly when expression of that gene is no longer desired or if it is desired to reduce that gene expression to a lower level. In this embodiment, expression could be blocked by the use of antisense molecules directed against the gene of interest. For example, see U.S. Pat. Nos. 5,728,558 and 5,741,684.

In further embodiments of the invention, antibodies are used to detect receptor expression in a cell. In preferred embodiments, detection is in transgenic plants and directed to assessing expression in various parts of the plant. Detection of the protein could be in situ by means of in situ hybridization of tissue sections but may also be analyzed by bulk protein purification and subsequent analysis by Western blot or immunological assay of a bulk preparation. Alternatively, gene expression can be expressed at the nucleic acid level by techniques well known to those of ordinary skill in any art using complimentary polynucleotides to assess the levels of genomic DNA, mRNA, and the like. As an example, PCR primers complimentary to the nucleic acid of interest can be used to identify the level of expression.

Plants of interest include, but are not limited to corn (*Zea mays*), canola (*Brassica napus, Brassica rapa* ssp.), alfalfa (*Medicago sativa*), rice (*Oryza sativa*), rye (*Secale cereale*), sorghum (*Sorghum bicolor, Sorghum vulgare*), sunflower (*Helianthus annuus*), wheat (*Triticum aestivum*), soybean (*Glycine max*), tobacco (*Nicotiana tabacum*), potato (*Solanum tuberosum*), peanuts (*Arachis hypogaea*), cotton (*Gossypium hirsutum*), sweet potato (*Ipomoea batatus*), cassava (*Manihot esculenta*), coffee (Cofea spp.), coconut (*Cocos nucifera*), pineapple (*Ananas comosus*), citrus trees (Citrus spp.), cocoa (*Theobroma cacao*), tea (*Camellia sinensis*), banana (Musa spp.), avocado (*Persea americana*), fig (*Ficus casica*), guava (*Psidium guajava*), mango (*Mangifera indica*), olive (*Olea europaea*), oats, barley, vegetables, ornamentals, and conifers. Preferably plants include corn, soybean, sunflower, safflower, Brassica, wheat, barley, rye, alfalfa, rice and sorghum. It is understood, however, that the invention encompasses embodiments in which host cells are other than plant cells in which a chimeric receptor contains an ecdysone ligand binding domain but heterologous domains derived from other types of cells, for example, invertebrate cells such as insects and fungi and animal cells such as avian and mammalian.

The compositions of the present invention are preferably used to transform plant. In this manner, genetically modified plants, plant cells, plant tissue, seed, and the like, can be obtained. By "transformed" is intended the stable introduction of DNA into the genome of the cell. Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) *Biotechniques* 4:320–334), electroporation (Riggs et al. (1986) *Proc. Natl. Acad. Sci. USA* 83:5602–5606, Agrobacterium-mediated transformation (Townsend et al., U.S. Pat No. 5,563,055), direct gene transfer (Paszkowski et al. (1984) *EMBO J.* 3:2717–2722), and ballistic particle acceleration (see, for example, Sanford et al., U.S. Pat. No. 4,945,050; Tomes et al., U.S. Pat. No. 5,879,918; Tomes et al., U.S. Pat. No. 5,886,244; Bidney et al., U.S. Pat. No. 5,932,782; Tomes et al. (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin); and McCabe et al. (1988) *Biotechnology* 6:923–926). Also see Weissinger et al. (1988) *Ann. Rev. Genet.* 22:421–477; Sanford et al. (1987) *Particulate Science and Technology* 5:27–37 (onion); Christou et al. (1988) *Plant Physiol.* 87:671–674 (soybean); McCabe et al. (1988) *Bio/Technology* 6:923–926 (soybean); Finer and McMullen (1991) *In Vitro Cell Dev. Biol.* 27P: 175–182 (soybean); Singh et al. (1998) *Theor. Appl. Genet.* 96:319–324 (soybean); Datta et al. (1990) *Biotechnology* 8:736–740 (rice); Klein et al. (1988) *Proc. Natl. Acad. Sci. USA* 85:4305–4309 (maize); Klein et al. (1988) *Biotechnology* 6:559–563 (maize); Tomes, U.S. Pat. No. 5,240,855; Buising et al., U.S. Pat. Nos. 5,322,783 and 5,324,646; Tomes et al. (1995) "Direct DNA Transfer into Intact Plant Cells via Microprojectile Bombardment," in *Plant Cell, Tissue, and Organ Culture: Fundamental Methods*, ed. Gamborg (Springer-Verlag, Berlin) (maize); Klein et al. (1988) *Plant Physiol.* 91:440–444 (maize); Fromm et al. (1990) *Biotechnology* 8:833–839 (maize); Hooykaas-Van Slogteren et al. (1984) *Nature* (London) 311:763–764; Bowen et al., U.S. Pat. No. 5,736,369 (cereals); Bytebier et al. (1987) *Proc. Natl Acad Sci. USA* 84:5345–5349 (Liliaceae); De Wet et al. (1985) in *The Experimental Manipulation of Ovule Tissues*, ed. Chapman et al. (Longman, N.Y.), pp. 197–209 (pollen); Kaeppler et al. (1990) *Plant Cell Reports* 9:415–418 and Kaeppler et al. (1992) *Theor. Appl. Genet.* 84:560–566 (whisker-mediated transformation); D'Halluin et al. (1992) *Plant Cell* 4:1495–1505 (electroporation); Li et al. (1993) *Plant Cell Reports* 12:250–255 and Christou and Ford (1995) *Annals of Botany* 75:407–413 (rice); Osjoda et al. (1996) *Nature Biotechnology* 14:745–750 (maize via *Agrobacterium tumefaciens*); all of which are herein incorporated by reference.

The cells which have been transformed may be grown into plants in accordance with conventional ways. See, for example, McCormick et al. (1986) *Plant Cell Reports* 5:81–84. These plants may then be grown, and either pollinated with the same transformed strain or different strains, and the resulting hybrid having the desired phenotypic characteristic identified. Two or more generations may be grown to ensure that the subject phenotypic characteristic is stably maintained and inherited and then seeds harvested to ensure the desired phenotype or other property has been achieved.

It is envisioned by the inventors that the system will be useful for selectively inducing the expression of specific proteins at a specific time in a plant's developmental cycle. A target gene or genes may be introduced that would enhance the nutritional value of a specific crop. The component could be induced just prior to harvest, or low doses of ligand could be administered throughout growth and development to create stores of a specific product. The system could also be used to selectively induce insecticidal properties or herbicide resistance. In the case of herbicide resistance, it is envisioned by the inventors that the ligand could be introduced to plants by spraying prior to the application of herbicides to clear otherwise unwanted competitors. The inventors further envision the use of the system in heightening plant resistance to environmental factors. Proteins could be selectively induced in response to inclement weather conditions to transiently enhance plant resistance to such conditions as cold, drought or soil over saturation.

It is envisioned that the use of tissue-preferred promoters known to those of skill in the art could limit inducibilty to specific tissues or cell types. The inventors envision regulating the expression of EcR and/or USP or their chimeric derivatives with tissue-preferred promoters. This combination will activate transcription of target sequences only in specific tissues or at specific developmental stages. The system could thus be used to selectively induce expression in the seed or in the reproductive structures of a plant with little or no expression in other areas of the organism. Thus products of expression could be compartmentalized in or away from areas that might be the subject of human consumption.

An embodiment of particular interest to the inventors is the use of the claimed invention in altering the fertility or system of reproduction in developing plants. The inventors envision the use of the ecdysone inducible expression system to promote or repress the expression of genes in tissues of plants that facilitate reproduction. One of skill in the art would recognize that specific genes are known that may be selectively induced or expressed in order to regulate the fertility or mode of reproduction of a given plant. For example, U.S. Pat. No. 5,432,068 teaches a method for controllably rendering plants male fertile by using an inducible promoter to regulate expression of a gene critical to male fertility such that when the gene is "off," the plant is sterile; however, when the promoter is induced, the plant becomes fertile. Therefore, one embodiment of the present invention is the use of the ecdysone inducible expression system to regulate male fertility in plants using such a method.

Further, to render the reproductive process ineffective, formation of viable zygotes can be prevented. This may be achieved through a variety of means, including for example, any disruption or alteration of a process that is critical to the formation of viable gametes. Male sterility may result from defects leading to either a lack of pollen formation or the production of pollen that is incapable of effective fertilization. Female sterility may result from the disruption of tissues required for the pollen germination, growth or fertilization. This may result from, for example, the failure to produce functional embryo sacs, ovaries, pistils, stigmas, or transmitting tracts. In addition, an alternative mode of reproduction is apomixis in which progenies are produced asexually using female floral components that have not undergone meiosis or normal double fertilization.

Target sequences encoding proteins of interest that would be useful in disrupting the fertilization process include, for example, Adenine Phosphoribosyltransferase (APRT) (Moffatt et al. (1988) *Plant Physiol.* 86: 1150–1154, ribonuclease from *Bacillus amyloliquefaciens* (Mariani et al. (1990) *Nature* 347:737–741), indole acetic acid-lysine synthetase from *Pseudomanas syringae* (Romano et al. (1991) Genes and Development 5: 438–446), pectate lyase pelE from *Erwinia chrysanthemi* EC16 (Keen et al. (1986) *J. Bacteriology* 168:595), Cyt A toxin from Bacillus thuringiensis israeliensis (McLean et al. (1987) *J. Bacteriology* 169: 1017–1023), T-urf13 from cms-T maize mitochondrial genomes (Braun et al. (1990) *Plant Cell* 2:153, gin recombinase from phage Mu (Maeser et al. (1991) *Mol. Gen. Genet.* 230:170–176), and diphteria toxin A-chanin (Greenfield et al.(1983) *Proc. Natl. Acad. Sci.* 80: 6853)

The inventors envision the transformation of plants with a target sequence encoding a protein of interest that disrupts the fertilization process. The use of anther or pistil preferred promoters to control expression of EcR and/or USP or their chimeric derivative ensures the expression of the target sequences in tissues that are necessary for fertility. The target sequences will therefore not be deleterious to other plant tissues.

For example, transgenic plants and plant cells may be transformed to contain multiple DNA constructs. The first DNA construct encodes an Ecdysone receptor or a chimeric derivative thereof. This DNA construct comprises an anther or pistil preferred promoter, an organism specific transcription activator, a DNA binding domain, and an EcR ligand-binding domain. The second DNA construct comprises an appropriate transcriptional response element operably linked to a constitutive promoter operably linked to a target sequence. Treatment of the transgenic plant with ecdysone would lead to expression of the target sequence and render the plant infertile.

In another embodiment, a third DNA construct is introduced into the plant, and comprises a tissue-preferred promoter operably linked to a USP coding sequence or a chimeric derivative thereof. In this embodiment, following treatment with ecdysone, expression of the DNA construct encoding the target sequence is regulated by the USP/EcR heterodimer.

The following examples are offered by way of illustration and not by way of limitation.

EXPERIMENTAL

EXAMPLE 1

Isolation of Ecdysone Receptor and Ultraspiracle

For library construction, total RNA was isolated from the European corn borer, Ostrinia nubilalis. Corn borer larvae (for example, a mix of stage 2, 3, and 4, equal weight) can be pulverized in liquid nitrogen, homogenized, and total RNA Aextracted by standard procedures. PolyA RNA was isolated from the total RNA using the PolyATact system from Promega Corporation, Madison, Wis. cDNA synthesis was performed and unidirectional cDNA libraries were constructed according to the ZAP Express cDNA synthesis kit from Stratagene, La Jolla, Calif. cDNA was amplified by PCR, sized and properly digested with restriction fragments to be ligated into a vector. Probes for the EcR and USP genes were isolated from the cDNA. The cDNA and the degenerate primers were combined in a PCR mix. After amplification, prominent bands were subcloned and sequenced and the fragments obtained can be used to probe for EcR or USP from the corn borer library. The primers used to amplify EcR were 5' CGG AAT TCG GNT AYC AYT AYA AYG C 3' (SEQ ID NO: 5), and 5' CCT CGG GACSAC TTC GTG AAT CC 3' (SEQ ID NO:6). For USP the following primers were used. 5' TGT GAR GGC TGC AAR GGS TTC TT 3' (SEQ ID NO: 7), and 5' GCC AGM GCG AGC AGC AG 3' (SEQ ID NO: 8). Subdloned cDNA was sequenced to identify sequences with the proper peptide identity corresponding to published sequences. These fragments were used to probe a cDNA library from *Ostrinia nubilalis* and a full length coding sequence was obtained. The coding sequence was ligated into an expression cassette and sequenced.

EXAMPLE 2

Transactivation of a Reporter Sequence by the Ecdysone and USP Receptors Using Transient Expression Assays To examine the effect of the Ecdysone and USP receptors on promoter-driven expression, a transient transactivation assay was developed using a cell suspension culture derived from maize embryos. (See also, U.S. Pat. No. 5,886,244) A reporter plasmid, designated PHP11545, was constructed in the pSP72 vector and contained 8 LexA operators, a minimal fragment of the CaMV-59 constitutive promoter, the Omegá leader sequence, Adh intron 1, the coding sequence for firefly luciferase, and the PinII terminator sequences.

Two DNA constructs encoding effector proteins were generated. A chimeric Ecdysone receptor construct designated PHP 10956 was generated. PHP10956 contains the Nopaline synthase (NOS) promoter, the Omegá leader sequence, Adh1 intron, and the potato protease inhibitor II (PinII) termination sequences cloned into a pUC vector. A fragment encoding a fusion between the maize C1 transactivation domain, the LexA DNA binding domain, and the ligand-binding domain of the Ecdysone receptor was cloned downstream of the intron.

A DNA construction containing the USP coding sequences was generated and designated PHP10967. PHP10967 contains the Nos promoter, the Omegá leader sequence, Adh1 intron, and the PinII terminator sequences cloned into the pUC vector. The nucleic acid sequence encoding the USP coding region was inserted downstream of the intron.

These constructs were introduced into embryogenic suspension cells by microprojectile bombardment as described by Unger et al. (1993) *The Plant Cell* 5:831–841. Plasmid DNA encoding effector and reporter sequences was mixed with 50 $\mu$l (15 mg/ml) of 1.0 $\mu$m tungsten microprojectiles. The concentration of the plasmids encoding the effector and reporter sequences is shown in Table 1. DNA was precipitated by addition of 50 $\mu$l 2.5 M $CaCl_2$ and 20 $\mu$l 0.1M spermidine. Microprojectiles and precipitated DNA were centrifuged to a pellet and the supernatant was removed. The pellet was washed by sonication in the presence of 250 $\mu$l absolute ethanol, centrifuged and ethanol removed. Sixty $\mu$l of fresh absolute ethanol was added and this mixture sonicated to disperse the pellet. Ten $\mu$l aliquots of this microprojectile-DNA mixture were placed on each macrocarrier and bombarded into maize suspension cells using a helium-driven microprojectile gun, PDS-1000 (1100 psi rupture disk pressure). Maintenance of embryogenic suspension cultures and transient expression assays were performed as previously described by Unger et al. (1993) *The Plant Cell* 5:831–841 and by U.S. Pat. No. 5,886,244.

TABLE 1

| Treatment | EcR ($\mu$g) | USP ($\mu$g) | PHP11545 ($\mu$g) |
|---|---|---|---|
| NosCLO only | PHP10956 (0.02) | none | 5 |
| NosCLO/NosUSP | PHP10956 (0.02) | PHP10697 (0.02) | 5 |
| Reporter only | none | none | 5 |

Following cobombardment of the reporter and effector plasmids into the embryogenic suspension cells the transactivation of the Luciferase reporter construction was assayed. Transient transformed callus tissue was incubated on filter paper soaked with water or media and with ligand or the ethanol carrier. For the transient assays, 50 mg of callus tissue was incubated in the presence of ligand (10 $\mu$M RH5992) or ethanol carrier control. The luciferase assays were performed as previously described (Unger et al. (1993) *The Plant Cell* 5:831–841) following 16 to 18 hours of incubation at 26° C.

Luciferase expression was measured in average light units and the results are summarized in Table 2. Expression of the USP receptor (plasmid PHP10967) and the C1::LexA::ecdysone fusion protein (plasmid PHP10956) transactivated the LexA responsive luciferase reporter (PHP11545) 53 fold in the presence of the RH5992 ligand (Table 2).

The USP receptor was not required for transactivation of the luciferase reporter. Expression of only the C1::LexA::ecdysone fusion protein (plasmid PHP10956) resulted in the transactivation of the LexA responsive luciferase reporter gene in the presence of the RH5992 ligand (Table 2).

TABLE 2

| Effector(s) | Effector Dose ($\mu$g) | RH5992 | Average Light Units | Fold Induction |
|---|---|---|---|---|
| NosCLO only | 0.02 | None | 18247 | — |
| NosCLO only | 0.02 | 10 $\mu$M | 153613 | 8.4x |
| NosCLO/NosUSP | 0.02 each | None | 3811 | — |
| NosCLO/NosUSP | 0.02 each | 10 $\mu$M | 201808 | 53x |
| Reporter only | None | None | 3843 | — |

EXAMPLE 3

Transactivation of a Reporter Sequence by a Chimeric Ecdysone Receptor

To further examine the effect of the Ecdysone receptors on promoter-driven expression, a stable transactivation assay was performed using a chimeric Ecdysone receptor. DNA constructs were generated for the expression of both effector and reporter DNA sequences.

A reporter plasmid, designated PHP1654, was constructed in the pSP72 vector and contained 5 GAL4 responsive elements, a minimal CaMV-59 constitutive promoter, the Omegá leader sequence, Adh intron 1, the coding sequence for firefly Luciferase, and the PinII terminator sequences.

Two DNA constructions encoding chimeric Ecdysone receptor proteins were generated. The chimeric Ecdysone receptor construct designated PHP10512 contains the Nopaline synthase (NOS) promoter, the Omega leader sequence, Adh1 intron, 35S promoter, PAT gene and the potato protease inhibitor II (PinII) termination sequences cloned into a pUC vector. A fragment encoding a fusion between the maize C1 transactivation domain, the Gal4 DNA binding domain, and the ligand-binding domain of the Ecdysone receptor was cloned downstream of the intron.

The plasmid designated PHP10513 also contains the Nopaline synthase (NOS) promoter, the Omega leader sequence, Adh1 intron, 35S promoter, PAT gene, and the potato protease inhibitor II (PinII) termination sequences cloned into a pUC vector. However, the fragment encoding the chimeric receptor immediately downstream of the intron, comprises a fusion between the VP16 activation domain, the Gal4 DNA binding domain, and the ligand-binding domain of the Ecdysone receptor.

Inmature embryos approximately 1.5 to 2.0 mm long from the Hi-II genotype (Armstrong and Phillips (1988) *Crop Sci.*

28:363–369) were bombarded with the PHP1654 reporter plasmid and either PHP10513 or PHP10512. As noted above, a selectable marker gene, PAT, was contained on PHP10513 and PHP10512. The PAT gene confers resistance to the herbicide Bialaphos. (Wohlleben et al. (1988) *Gene* 70:25–37.)

Embryos were bombarded using the protocols described in Tomes et al. (1994) *Plant Cell, Tissue, and Organ culture, Fundamental Methods* 197–213. Specifically, the Hi-II immature embryos were bombarded and cultured on selection medium as described by Songstad et al. 1993 *Agronomy Abstracts* 183. Plant regeneration from transgenic calli was performed according to the protocol of Armstrong and Phillips (1988) *Crop Sci* 28:363–369, except that bialaphos (3 mg/l) was added to each of the regeneration media. Plants were established in the greenhouse.

The transactivation of the luciferase reporter sequence by a chimeric Ecdysone receptor was assayed using standard protocols. Four leaf punches from each individual $T_0$ plant were placed on filter paper saturated with $H_2O$ (w/EtOH carrier) or 10 μM RH5992 in $H_2O$. Samples were incubated 16 hours and assayed for Luciferase activity. Results are shown in Light Units from both a negative control (i.e. leaf punches saturated with $H_2O$) and RH5992-induced samples of 20 μl of 200 μl total extract assayed from individual plants. The results are shown in Table 3.

TABLE 3

| Plasmid | Event Number | Sample Identification Number | Negative Control (Light Units) | RH5992 treated (Light Units) |
|---|---|---|---|---|
| PH10513 | 30 | 633295 | 140 | 37955 |
| | | 633296 | 146 | 38507 |
| | | 633297 | 153 | 37855 |
| | | 633298 | 128 | 42346 |
| | | 634477 | 129 | 38093 |
| | | 634478 | 113 | 26394 |
| | | 634479 | 136 | 24632 |
| | | 634480 | 120 | 33636 |
| | | 634481 | 129 | 28213 |
| | | 634482 | 95 | 22137 |
| | | 641482 | 505 | 105341 |
| | | 642456 | 124 | 44639 |
| | | 642457 | 348 | 49279 |
| | | 642458 | 203 | 83241 |
| | | 642459 | 609 | 61320 |
| | | 642460 | 281 | 130618 |
| | | 642461 | 324 | 95166 |
| | | 645018 | 171 | 35641 |
| PHP10512 | 78 | 645023 | 84 | 3771 |
| | | 645024 | 86 | 1819 |
| | | 645025 | 174 | 7742 |

TABLE 3-continued

| Plasmid | Event Number | Sample Identification Number | Negative Control (Light Units) | RH5992 treated (Light Units) |
|---|---|---|---|---|
| | | 645026 | 154 | 1027 |
| | | 645027 | 139 | 9742 |
| | | 645028 | 120 | 2486 |
| | | 645029 | 203 | 8494 |
| | | 645030 | 75 | 3988 |
| | | 645031 | 91 | 9265 |
| | | 645032 | 242 | 6198 |
| | | 645033 | 87 | 6293 |
| | | 645034 | 101 | 1045 |
| | | 645036 | 176 | 8354 |
| | | 645037 | 84 | 4720 |
| PHP10513 | 44 | 634930 | 17076 | 605147 |
| | | 634931 | 45065 | 528950 |
| | | 634932 | 15814 | 303021 |
| | | 642462 | 36795 | 573842 |
| | | 642463 | 7111 | 417072 |
| | | 645019 | 11959 | 511220 |
| | | 645020 | 15346 | 290095 |
| PHP10513 | 117 | 652405 | 2122 | 90037 |
| | | 652406 | 5711 | 40005 |
| | | 652407 | 2988 | 149594 |
| | | 652408 | 674 | 75379 |
| | | 652409 | 2315 | 49243 |
| | | 652410 | 3201 | 114913 |
| | | 652411 | 203 | 57607 |
| | | 652412 | 729 | 46075 |

The results of the stable transactivation assays show that expression of a chimeric Ecdysone receptor comprising the DNA binding domain of GAL4, the ligand binding domain of the Ecdysone receptor, and either the transactivation domain from Maize C1 or VP16 can activate transcription of the appropriate target sequences in the presence of an Ecdysone receptor ligand.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A method of selectively inducing gene expression of a nucleotide sequence of interest in a plant, said method comprising:
 a) stably incorporating into the genome of said plant a first expression cassette, said first expression cassette comprising a first promoter operably linked to a first nucleotide sequence that encodes a first protein and is selected from the group consisting of:
  i) a nucleotide sequence comprising the sequence set forth in SEQ ID NO: 1;
  ii) a nucleotide sequence comprising nucleotides 368–2005 of SEQ ID NO:1; and,
  iii) a nucleotide sequence encoding a polypeptide comprising the amino acid sequence set forth in SEQ ID NO:2;
 b) stably incorporating into the genome of said plant a second expression cassette, wherein said second expression cassette comprises a transcriptional regulatory region operably linked to a target sequence;
 c) stably incorporating into the genome of said plant a third expression cassette comprising a promoter operably linked to a third nucleotide sequence that encodes a second protein and is selected from the group consisting of:
  1) a nucleotide sequence comprising the sequence set forth in SEQ ID NO: 3;
  2) a nucleotide sequence comprising nucleotides 224–1603 of SEQ ID NO:3; and
  3) a nucleotide sequence encoding a polypeptide comprising the amino acid sequence set forth in SEQ ID NO: 4; and
 d) contacting said plant with a ligand that binds to at least one of said proteins to form a ligand-protein complex, wherein said ligand-protein complex interacts with said transcriptional regulatory region to induce gene expression of said target sequence.

2. The method of claim 1, wherein said plant is a dicot.

3. The method of claim 1, wherein said plant is a monocot.

4. The method of claim 3, wherein said monocot is maize.

5. The method of claim 1, wherein said ligand-protein complex comprises heterodimers of said first protein and said second protein.

6. A plant or its parts having stably incorporated in its genome:
 a) a first expression cassette comprising a first promoter operably linked to a first nucleotide sequence that encodes a first protein and is selected from the group consisting of:
  i) a nucleotide sequence comprising the sequence set forth in SEQ ID NO: 1;
  ii) a nucleotide sequence comprising nucleotides 368–2005 of SEQ ID NO:1; and
  iii) a nucleotide sequence encoding a polypeptide comprising the amino acid sequence set forth in SEQ ID NO: 2;
 b) a second expression cassette comprising a transcriptional regulatory region operably linked to a target sequence, wherein said transcriptional regulatory region is activated by a ligand-protein complex;
 c) a third expression cassette comprising a promoter operably linked to a third nucleotide sequence that encodes a second protein and is selected from the group consisting of:
  1) a nucleotide sequence comprising the sequence set forth in SEQ ID NO: 3;
  2) a nucleotide sequence comprising nucleotides 224–1603 of SEQ ID NO:3; and
  3) a nucleotide sequence encoding a polypeptide comprising the amino acid sequence set forth in SEQ ID NO: 4.

7. A plant cell having stably incorporated in its genome:
 a) a first expression cassette comprising a first promoter operably linked to a first nucleotide sequence that encodes a protein and is selected from the group consisting of:
  i) a nucleotide sequence comprising the sequence set forth in SEQ ID NO: 1;
  ii) a nucleotide sequence comprising nucleotides 368–2005 of SEQ ID NO:1; and
  iii) a nucleotide sequence encoding a polypeptide comprising the amino acid sequence set forth in SEQ ID NO: 2;
 b) a second expression cassette comprising a transcriptional regulatory region operably linked to a target sequence, wherein said transcriptional regulatory region is activated by a ligand-protein complex; and
 c) a third expression cassette comprising a promoter operably linked to a third nucleotide sequence that encodes a protein and is selected from the group consisting of:
  1) a nucleotide sequence comprising the sequence set forth in SEQ ID NO: 3;
  2) a nucleotide sequence comprising nucleotides 224–1603 of SEQ ID NO:3; and
  3) a nucleotide sequence encoding a polypeptide comprising the amino acid sequence set forth in SEQ ID NO: 4.

8. A transformed seed of a plant having stably incorporated in its genome:
   a) a first expression cassette comprising a first promoter operably linked to a first nucleotide sequence that encodes a first protein and is selected from the group consisting of:
      i) a nucleotide sequence comprising the sequence set forth in SEQ ID NO: 1;
      ii) a nucleotide sequence comprising nucleotides 368–2005 of SEQ ID NO:1; and
      iii) a nucleotide sequence encoding a polypeptide comprising the amino acid sequence set forth in SEQ ID NO: 2;
   b) a second expression cassette comprising a transcriptional regulatory region operably linked to a target sequence, wherein said transcriptional regulatory region is activated by a ligand-protein complex;
   c) a third expression cassette comprising a promoter operably linked to a third nucleotide sequence that encodes a second protein and is selected from the group consisting of:
      1) a nucleotide sequence comprising the sequence set forth in SEQ ID NO: 3;
      2) a nucleotide sequence comprising nucleotides 224–1603 of SEQ ID NO:3; and
      3) a nucleotide sequence encoding a polypeptide comprising the amino acid sequence set forth in SEQ ID NO: 4.

* * * * *